(12) United States Patent
Eibl

(10) Patent No.: US 7,351,428 B2
(45) Date of Patent: *Apr. 1, 2008

(54) PHOSPHATIDYL OLIGOGLYCEROLS

(75) Inventor: Hans-Jörg Eibl, Bovenden (DE)

(73) Assignee: Max-Planck-Gesselschaft zur Forderung der Wissenschaften E.V., Munich (DE)

( * ) Notice: Subject to any disclaimer, the term of this patent is extended or adjusted under 35 U.S.C. 154(b) by 55 days.

This patent is subject to a terminal disclaimer.

(21) Appl. No.: 10/840,607

(22) Filed: May 7, 2004

(65) Prior Publication Data

US 2004/0213836 A1    Oct. 28, 2004

Related U.S. Application Data

(60) Continuation of application No. 10/095,970, filed on Mar. 13, 2002, now abandoned, which is a division of application No. 09/125,276, filed as application No. PCT/EP97/00749 on Feb. 17, 1997, now Pat. No. 6,413,543.

(30) Foreign Application Priority Data

Feb. 16, 1996  (DE) ................. 196 05 833
Jun. 3, 1996   (DE) ................. 196 22 224

(51) Int. Cl.
    *A61K 9/127*  (2006.01)
(52) U.S. Cl. ................ 424/450; 514/75; 514/78; 554/78; 554/79
(58) Field of Classification Search ............ 514/75, 514/78; 424/450; 554/78, 79
    See application file for complete search history.

(56) References Cited

U.S. PATENT DOCUMENTS

| 5,250,290 A | 10/1993 | Giacomoni et al. |
| 5,290,565 A | 3/1994 | Zysman et al. |
| 5,362,494 A | 11/1994 | Zysman et al. |
| 6,413,543 B1 * | 7/2002 | Eibl .................. 424/450 |

FOREIGN PATENT DOCUMENTS

| DE | 3427093 | 2/1985 |
| DE | 240020 | 10/1986 |
| DE | 3619883 | 12/1986 |
| EP | 0071019 | 2/1983 |
| JP | H04-268397 | 9/1992 |
| JP | H08-12519 | 1/1996 |
| JP | 11-080749 | 3/1999 |

OTHER PUBLICATIONS

Maruyama et al, International Journal of Pharmaceutics, 1994, 111(1), 103-7.*
Maruyama et al., 1994, CAS:121:212789.*
Lesieur, "Chemistry and Physics of Lipids," 56:109-121, 1990.
T.M. Allen, "Stealth Liposomes: Five Years On," *Journal of Liposome Research* 2(3):289-305, Jan. 1992.
Maruyama et al., "Phosphatidyl polyglycerols prolong liposome circulation in vivo," *International Journal of Pharmaceutics* 111:103-110, 1994.
Baig et al., "Steroselective Total Synthesis of (2R.2'S.3Z) -1-0-(2-Mehtoxyhexadeceny) glycerol and (2R.2'S)-1-(2'-Methoxyhexadecyl) glycerol-Potential Antitumour compounds from shark liver oil," *Tetrahedron* 51(16):4723-4732, 1995.
S. Baskaran et al., "An Efficient and Stereoselective Synthesis of (2R.2'S)-1-O-(2'-hydroxy-hexadecyl) glycerol and Its Oxo Analogs: Potential Antitumour Compounds From Shark Liver Oil," *Tetrahedron* 52(18):6437-6452, 1996.
I. Uchegbu et al., "Large Disk-Shaped Structures (Discomes) In Nonionic Surfactant Vescicle to Micelle Transitions," *J. Phys. Chem.* 96:10548-10553, 1992.

* cited by examiner

*Primary Examiner*—Rei-tsang Shiao
(74) *Attorney, Agent, or Firm*—Rothwell Figg Ernst & Manbeck, P.C.

(57) ABSTRACT

In order to form liposomes with a longer half-life in blood, use is made of defined formula (A)

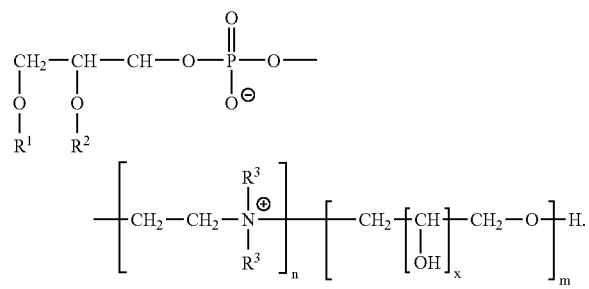

12 Claims, 3 Drawing Sheets

THE LIPOSOME DISTRIBUTION IN THE ORGANS WAS DETERMINED 72 H AFTER I.V. ADMINISTRATION. PALE BARS: SPLEEN; DARK BARS: LIVER. SUVs: SMALL UNILAMELLAR LIPOSOMES OF APPROX. DIAMETER 60 nm; LARGE UNILAMELLAR LIPOSOMES OF APPROX. DIAMETER 190nm.

PHOSPHATIDYL OLIGOGLYCEROLS

CROSS REFERENCE TO RELATED APPLICATIONS

This application is a continuation application of U.S. application Ser. No. 10/095,970, filed Mar. 13, 2002, now abandoned which is a divisional application of U.S. application Ser. No. 09/125,276, filed Nov. 20, 1998, now U.S. Pat. No. 6,413,543, which is a national stage filing under 35 U.S.C. § 371 of PCT/EP97/00749, filed Feb. 17, 1997. This application further claims priority under 35 U.S.C. § 119 to foreign applications 19605833.3 (DE), filed Feb. 16, 1996, and 19622224.9 (DE), filed Jun. 3, 1996. The disclosures of all of the above identified applications are hereby incorporated by reference.

The invention relates to phosphatidyl compounds which contain a defined hydrophilic residue, and to long-circulating liposomes.

Conventional liposomes circulate in the serum for up to 5 hours. However, especially when liposomes are used as a means of drug delivery, it is desirable that they circulate in the bloodstream for as long as possible.

To this end, the so-called "stealth liposomes" were developed, which are not destroyed in the bloodstream so quickly. These "stealth liposomes" are built up on the basis of phosphatidyl compounds which have an extended polyethylene glycol residue. The polyethylene glycol residue proved to be most effective in producing the desired increase in liposome survival duration when the molecular weight was between 2000 and 3000. A serious disadvantage, however, of these "stealth-liposomes", ie, of these phosphatidyl compounds with a polyethylene glycol residue, is that the compounds are not exactly defined, since the polyethylene glycol residues display different chain lengths.

Maruyama et al. (Int. J. Pharmac. 111 (1994), 103-107) suggested the use of dipalmitoyl phosphatidyl polyglycerols to lengthen the duration of liposome circulation. However, since technical-grade polyglycerols were used as starting material, no uniform products were obtained here either. Technical polyglycerols, which consist of a mixture of polyglycerols with different chain lengths and monoglycerol, and which are characterized by their average molecular weight, were phosphatidylated by means of phospholipase D. The resulting products only led to a small increase in the survival duration of liposomes in the blood.

The object of this invention was thus to provide compounds which increase the survival duration of liposomes and which are of exactly definable composition.

This objective is established according to the invention by means of a compound with the general formula (A)

where $R^1$ and $R^2$, independent of each other, stand for hydrogen or a saturated or unsaturated alkyl or acyl residue, which may be branched and/or substituted, $R^3$ stands for hydrogen or an alkyl residue, n=0 or 1,
x is a whole number from 1 to 4 and
m is a whole number from 2 to 10 if n=0, or a whole number from 1 to 10 if n=1, or 1 if x is greater than 1, and where, in the case that n=0, the compound is more than 90% uniform with respect to the value of m.

The stepwise synthesis—upon which this invention is based—of the hydrophilic residues of the phosphatidyl compounds of formula (A) makes it possible to obtain compounds of an exactly defined composition.

The compound of the invention, with the formula (A), is thus not a mixture of various molecules of indefinite composition and chain length, but can be synthesized to have precisely the desired structure. If, for example, the desired product is a triglycerol derivative, ie, x=1 arid m=3 in formula (A), the content of monoglycerol, diglycerol, tetraglycerol and higher oligoglycerol derivatives will be low. It is preferable if a glycerol derivative of a certain chain length is obtained that is largely free of glycerol derivatives of other chain lengths. The content of monoglycerol derivatives, in particular, is low, amounting to less than 5%, preferably less than 1% or, even more preferably, less than 0.1% relative to the desired oligoglycerol derivative.

According to the invention, the compound of formula (A) is a uniform compound of defined structure. It is of advantage if, with respect to the value of m, the compound is greater than 95% uniform. It is to greater advantage if it is more than 99% uniform. It is even possible to provide a compound which is more than 99.9% uniform with respect to the value of m.

The compound is preferably an oligoglycerol derivative with 2 to 5 glycerol units, more preferably with 2 to 4 glycerol units. It is to advantage if these are 1.3-linked linear oligoglycerol residues.

According to the invention, the residues $R^1$ and $R^2$, independent of each other, stand for hydrogen, a saturated or unsaturated $C_1$-$C_{24}$ alkyl or $C_1$-$C_{24}$ acyl residue, preferably hydrogen or a saturated or unsaturated $C_8$-$C_{24}$ alkyl or $C_8$-$C_{24}$ acyl residue, it being beneficial if it at least one of the residues $R^1$ and $R^2$ is an acyl residue.

The residue $R^3$ is preferably hydrogen or an alkyl residue with 1 to 4 carbon atoms.

The compound of formula (A) can be a racemic compound which contains a phospho-rac-(1 or 3)-oligoglycerol linkage, or it can be in the form of a stereospecific isomer. The stereoisomers can have a phospho-sn-1-oligoglycerol linkage or a phospho-sn-3-oligoglycerol linkage. The formation of the stereospecific linkage can be carried out in a manner analogous to those described in the literature (DE 31 30 867 A1; H. Eibl et al., Chem. Phys. Lipids, 28 (1981), 1-5, 41 (1986), 53-63 and 47 (1988, 47-53).

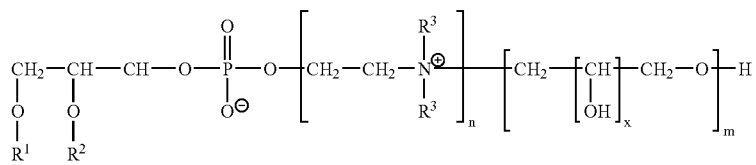

The subject matter of the invention also includes liposomes which contain phospholipids and/or alkyl phospholipids, maybe cholesterol, and 1 to 50 mol % of a compound with the general formula (A),

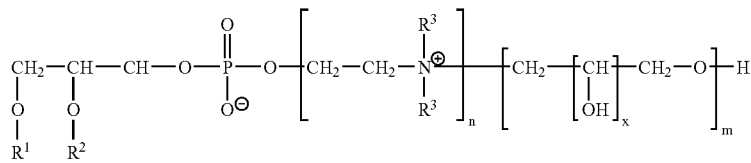

or salts thereof, where the cholesterol, the phospholipids, the alkyl phospholipids and the compound of formula (A) together make up 100 mol %, and $R^1$ and $R^2$, independent of each other, stand for hydrogen, a saturated or unsaturated alkyl or acyl residue which may be branched and/or substituted, $R^3$ stands for hydrogen or an alkyl residue, n=0 or 1, x is a whole number from 1 to 4 and m is a whole number from 2 to 10 if n=0, or a whole number from 1 to 10 if n=1, or 1 if x is greater than 1, and where, in the case that n=0, the compound (A) is more than 90% uniform in respect of the value of m.

The liposomes of the invention have a half-life in serum of up to 18 to 20 hours. Surprisingly, the liposome concentration in blood was found to decrease linearly.

It is beneficial according to the invention if compound (A) displays a uniformity of more than 95% or, even better, more than 99% with respect to the value of m. It is also possible, however, to use compound (A) in practically pure form, ie, more than 99.9% uniform with respect to the value of m.

The liposomes preferably contain a compound of formula (A), in which x=1 and m is a whole number from 2 to 5; it is even more preferable if m is a whole number from 2 to 4.

The residues $R^1$ and $R^2$ of the compound of formula (A) contained in the liposomes can stand, independent of each other, for hydrogen or a saturated or unsaturated $C_1$-$C_{24}$ alkyl or $C_1$-$C_{24}$ acyl residue, preferably hydrogen or a saturated or unsaturated $C_8$-$C_{24}$ alkyl or $C_8$-$C_{24}$ acyl residue. The substituent is a residue which does not interfere during the preparation. $R^3$ is preferably hydrogen or a $C_1$-$C_4$ alkyl residue.

The compound of formula (A) can be present in the liposomes as a racemic mixture, ie, with a phospho-rac-(1 or 3)-oligoglycerol linkage. It is preferable if it is present in stereospecific form with a phospho-sn-1-oligoglycerol linkage or a phospho-sn-3-oligoglycerol linkage.

It is to advantage if at least one of the residues $R^1$ and $R^2$ of formula (A) is an acyl group.

It is beneficial if liposomes containing the compound of formula (A) with n=0 exhibit an excess negative charge. However, liposomes can also be prepared from compounds of formula (A) in which n=1. In this case, it is better if the liposomes exhibit no excess charge or a positive one.

Besides a compound of formula (A), the liposomes contain phospholipids and/or alkyl phospholipids and maybe cholesterol. It is preferable to use the compound of formula (A) in an amount of 5 to 15 mol %. If the liposomes do not display an excess charge, a composition of 0 to 70 mol % cholesterol, 1 to 50 mol % of a compound of formula (A), and phospholipids and/or alkyl phospholipids is preferred. If there is a negative excess charge, a preferred liposome composition consists of 0 to 70 mol % cholesterol, 1 to 15 mol % of a compound of formula (A), and phospholipids and/or alkyl phospholipids. A higher proportion of compounds of formula (A) with a negative excess charge would lead to instability of the liposomes in the blood circulation. It is to advantage if the liposomes comprise 35 to 43 mol %, in particular 38 to 42 mol % cholesterol, 5 to 15 mol % of a compound of formula (A), and phospholipids and/or alkyl phospholipids.

The phospholipids and/or alkyl phospholipids can, for example, be diacyl phospho-glycerols of defined structure. Generally speaking, these lipid components can be used as compounds of defined structure.

In the case that x>1, it is preferable if the residue —$CH_2$(—CHOH)$_x$—$CH_2OH$ derives from sugar alcohols which have four hydroxyl groups for x=2, five hydroxyl groups for x=3, and 6 hydroxyl groups for x=4. Examples of such residues are mannitol derivatives for x=4, lyxitol derivatives for x=3 and threitol derivatives for x=2.

The liposomes of the invention have a markedly longer half-life in the blood stream. Their half-life is preferably at least 10 hours, better still, more than 12 hours. Half-lives of 18 to 20 hours have been measured for the liposomes of the invention. Surprisingly, the decrease in blood lipid concentration with time was found to be absolutely linear. It is preferable according to the invention if, after 6 hours, more than 50% of the liposomes added are still present in the blood; it is even more preferable if more than 60% are still present.

A particularly surprising property of the liposomes of the invention is their preferred tendency to accumulate in the spleen. Depending on the composition and size of the liposomes, enrichment thereof in the spleen has been found which exceeds enrichment in the liver by a factor of 25. Enrichment in the spleen compared with that in the liver increases with increasing value of m in formula A and with increasing size of the liposomes. With the transition from SUVs (Small Unilamellar Liposomes; diameter about 60 nm) to LUVs (Large Unilamellar Liposomes; diameter about 190 nm), the degree of enrichment in the spleen increases many times over. The preferential accumulation in the spleen also increases as the number of carbon atoms in $R^1$ and $R^2$ increases.

It was found, in addition, that the liposomes of the invention also accumulate in certain tumour tissues. This was observed to be the case, for example, with breast carcinomas induced by nitrosomethylurea (MNU carcinoma).

The liposomes of the invention can also contain one or more pharmaceutical drugs.

Generally speaking, all drugs can be used that can be introduced into the plasma by means of liposomes. Preferred groups of drugs are, on the one hand, cytostatic agents, especially anthracycline antibiotics such as doxorubicin, epirubicin and daunomycin, with doxorubicip being especially preferred. Other preferred anti-tumour drugs are idanibicin, hexadecylphosphocholine, 1-octadecyl-2-methyl-rac-glycero-3-phosphocholine, 5-fluoruracil, cis-platinum complexes such as carboplatin and novantron, and mitomycins.

Other preferred groups of drugs are immunomodulating substances such as citokines, of which interferon and, in particular, α-interferon are given special preference, antimycotic substances (eg, amphotericin B), and drugs to combat protozoan diseases (malaria and trypanosome and leishmania infections). Taxol is another preferred drug.

Yet another group of preferred drugs is the group of lytic drugs, as are described in the DE 41 32 345 A1. The content of this patent application is thus included by way of reference. Preferred drugs are miltefosin, edelfosin, ilmofosin and SRI62-834.

The subject matter of the invention thus includes use of the liposomes according to the invention for preparing an anti-tumour agent, with the drug doxorubicin being given special preference.

The subject matter of the invention also includes use of the liposomes according to the invention for preparing an agent to influence cell proliferation, with the drug preferably being a cytokine, in particular α-interferon.

The subject matter of the invention includes, in addition, a pharmaceutical composition which contains the liposomes described above and, entrapped in the liposomes, one or more pharmaceutical drugs, combined if necessary with standard pharmaceutical diluents, adjuvants, carrier media and fillers.

The liposomes of the invention are prepared using methods which are known per se and with the usual equipment. Typically, a solution containing the various components of the liposome and 1 to 50 mol % of a compound of formula (A) is converted into a lipid suspension which is then pressed under high pressure through nozzles or a perforated disk; the size of the liposomes can be regulated by means of the size of the perforations in the disk. Suitable measures for converting a lipid suspension into liposomes are familiar to persons versed in the art. Preferably, 5 to 15 mol % of a compound of the general formula (A), 35 to 43 mol % cholesterol and 42 to 60 mol % phospholipids and/or alkyl phospholipids are converted into a lipid suspension, which in turn is converted into liposomes by means of suitable measures and in a manner known per se.

These known methods can also be used to make a pharmaceutical formulation which contains the liposomes of the invention and one or more pharmaceutical drugs. To entrap water-insoluble drugs, the drug is dissolved together with the lipid components, while to entrap water-soluble drugs, an aqueous solution which contains the water-soluble drug is added to the lipid film.

The compounds of the invention, having the formula (A), can be prepared in cases where n=1 by linking a defined oligoglycerol with a phosphatidyl ethanolamine by way of the amino group. This results in neutral compounds, ie, compounds without an excess charge. The defined oligoglycerols used for linking are compounds with the formula (B).

In cases where n=0, compounds with the general formula (A) are made by linking a defined oligoglycerol with a phosphatidylglycerol. When n=0, compounds with the general formula (A) can also be made—using a phosphorylation agent—by linking a defined oligogycerol or a $C_4$-$C_6$ sugar alcohol with an alcohol of the formula $CH_2$—$OR^1$—$CHOR^2$—$CHOH$. As phosphorylation agent, use is made preferably of $POCl_3$.

The preparation of phospholipids from diacyl glycerols is described in the literature (DE 32 39 817 A1; P. Woolley et al., Chem. Phys. Lipids 47 (1988), 5562; H. Eibl et al., Chem. Phys. Lipids 47 (1988), 63-68), and this method can be applied here.

Using the above-described methods, a racemic compound is formed which contains a phospho-rac-(1 or 3)-oligoglycerol linkage. It is to advantage if stereospecific compounds are formed, which exhibit a phospho-sn-1-oligoglycerol linkage or a phospho-sn-3-oligoglycerol linkage. To make a compound of formula (A), it is preferable to use a linear oligoglycerol of defined chain length.

The subject matter of the invention also includes a protected oligoglycerol of the formula (B),

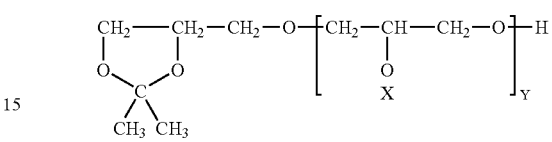

where Y is a whole number from 1 to 9 and X is a benzyl, alkyl or tetrahydropropanyl group. It is beneficial if Y is a whole number from 1 to 3. It is possible according to the invention to obtain 1.3-linked oligoglycerols in practically pure form. Oligoglycerols of a predefined chain length can be prepared which contain hardly any impurities in the form of oligoglycerols with different chain lengths. In addition, these oligoglyerols of the invention are practically free of monomeric glycerol. In other words, uniform compounds are obtained, which have a defined structure.

In the oligoglycerol, X can also stand for a different suitable protective group. It is also possible to replace the acetone with another protective group, in particular another ketone.

The invention comprises, in addition, alkyl oligoglycerols of formula (C)

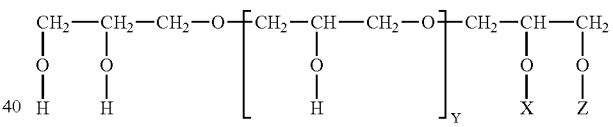

where Y is a whole number from 0 to 8, preferably a whole number from 1 to 3, and one of the residues X or Z is a saturated or unsaturated alkyl residue and the other residue is hydrogen. These alkyl oligoglycerols are also uniform compounds of defined structure.

The production of oligoglycerols, protected oligoglycerols and alkyl oligoglycerols is of particular interest, because with the help of these starting materials a number of important and novel adjuvants serving as solubilizers and to improve membrane permeation are obtained. Of particular interest with respect to increasing the period for which the liposomes survive in the blood stream is the production of phosphatidyl oligoglycerol derivatives of formula (A), which carry additional hydroxyl groups in the polar area.

Due to the preferred enrichment of the liposomes of the invention in the spleen, these liposomes are suitable generally for the selective introduction of substances into the spleen. These substances may be medicinal products, contrast agents or the like. This is especially important with regard to improving the quality of vaccines, since the spleen plays a major role in the formation of antibodies for the immune system. In the same way, the enrichment of the liposomes according to the invention such as was observed in tumour tissue is of importance with regard to delivering drugs, contrast agents and the like specifically to such tissue.

The following examples, together with the enclosed drawings, explain the invention in more detail. In the drawings.

EXAMPLE 1

In an animal experiment, liposomes were used which consisted of 40 mol % cholesterol, 10 mol % phosphatidylglycerol and 50% dipalmitoyl lecithin. The liposomes had a half-life in serum of 4 hours, with a typical persistence characteristic, ie, a rapid decrease to start with, followed by a slower decrease.

Liposomes of the same composition were prepared, in which the phosphatidylglycerol was replaced by a phosphatidylglycerol G2 of the invention. A half-life in serum of 18 to 20 hours was measured, the decrease with time being absolutely linear. This linear relation was observed irrespective of the size of the liposomes. The same linear reduction in serum liposome concentration was found with 50 nm liposomes and with 150 nm liposomes. The linear reduction in blood liposome concentration was also observed for different starting concentrations.

EXAMPLE 2

Percentage of Liposomes in the Blood Stream After 6 Hours

Liposomes according to the invention were prepared, consisting of dipalmitoyl-sn-G-3-PC/cholesterol/dipalmitoyl-sn-G-3-PG$_y$ in a molar ratio of 45:45:10. The percentages of liposomes still in the blood after 6 hours are listed in Table 1. For comparison, the percentages measured by Maruyama et al. under the same conditions for the system distearyl-sn-G-3-PC/cholesterol/dipalmitoyl-sn-G-3-PG$_n$ 45:45:10 are listed too. Compared to the prior art, the example of the invention shows a pronounced increase in the quantity of liposomes found.

TABLE 1

| Y | Comparative example | Y | Example of the invention |
|---|---|---|---|
| 0 | 18% | 0 | 21% |
| 2 | 19% | 2 | 80% |
| 3 | — | 3 | 82% |
| 4 | 20% | 4 | 56% |

EXAMPLE 3

Figure 1:
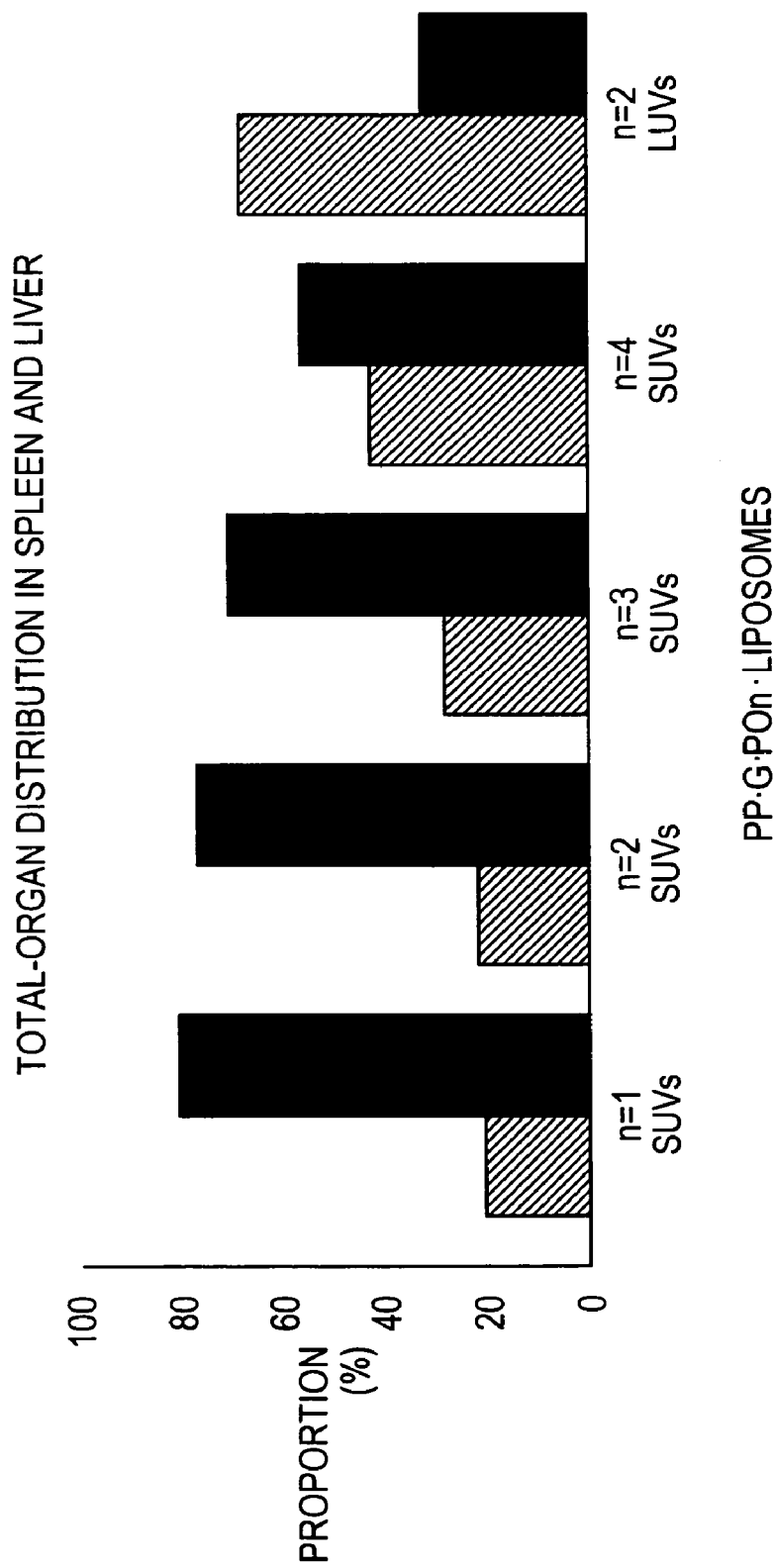
FIG. 1 shows the total-organ distribution of liposomes according to the invention in the spleen and in the liver.

Liposomes consisting of 1,2-dipalmitoyl-sn-glycero-3-phosphocholine, 1,2-dipalmitoyl-sn-glycero-3-phosphoglyceroglycerol (PG$_n$) and cholesterol in a molar ratio of 4:1:5 were doped with tritium-labelled inulin. These liposomes were administered to rats in a dosage of 100 μmol lipid per kg rat, and after 72 hours the distribution of these liposomes in the spleen and the liver was determined by measuring the radioactivity. Liver weights varied between 9 and 10 g, those of the spleen between 0.6 and 0.7 g. FIG. 1 of the enclosed drawings shows that for a liver weight which is about 15 times higher than that of the spleen, the distribution of liposomes (SUVs) increases substantially in favour of the spleen as the number of glycerol units increases (x=1; m=1 to 4 in formula A).

Figure 2:
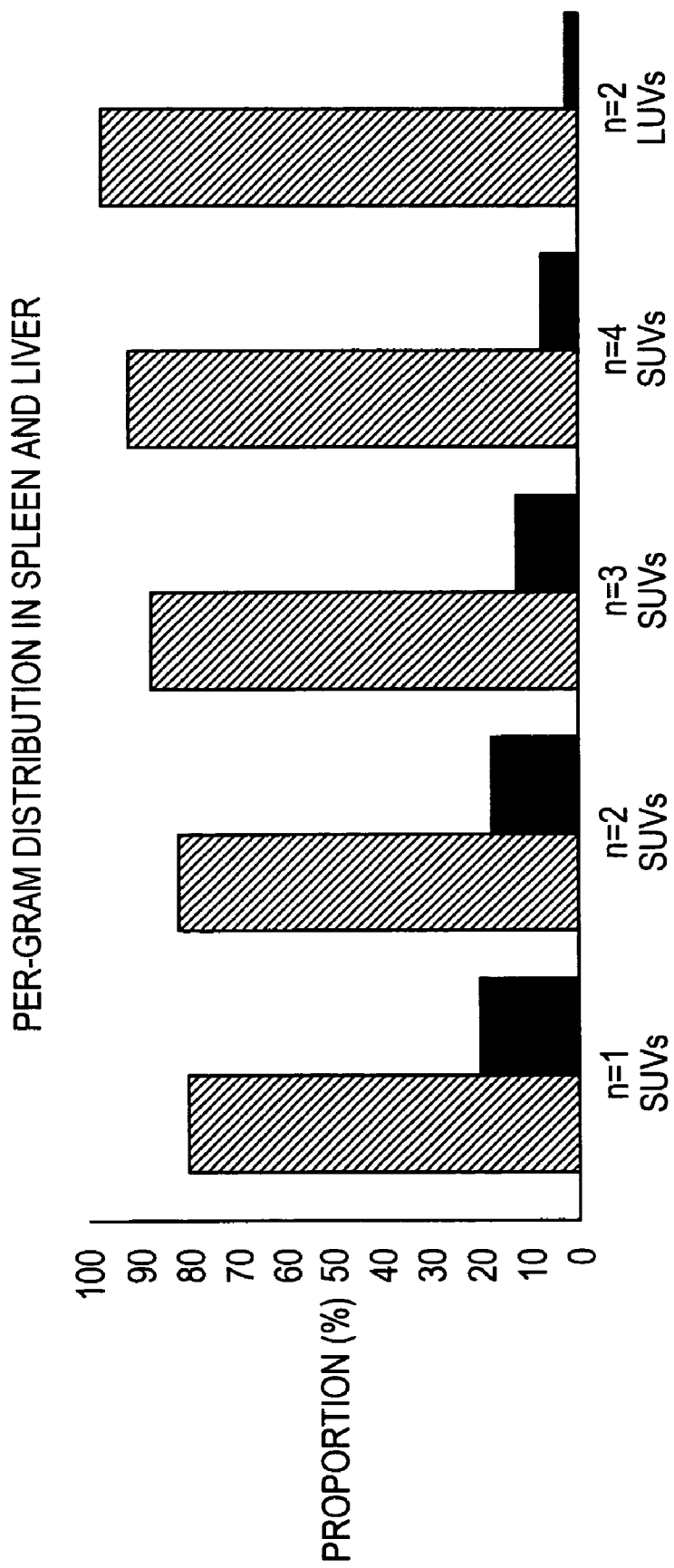
FIG. 2 shows the per-gram distribution of liposomes according to the invention in the spleen and in the liver.
Figure 3:
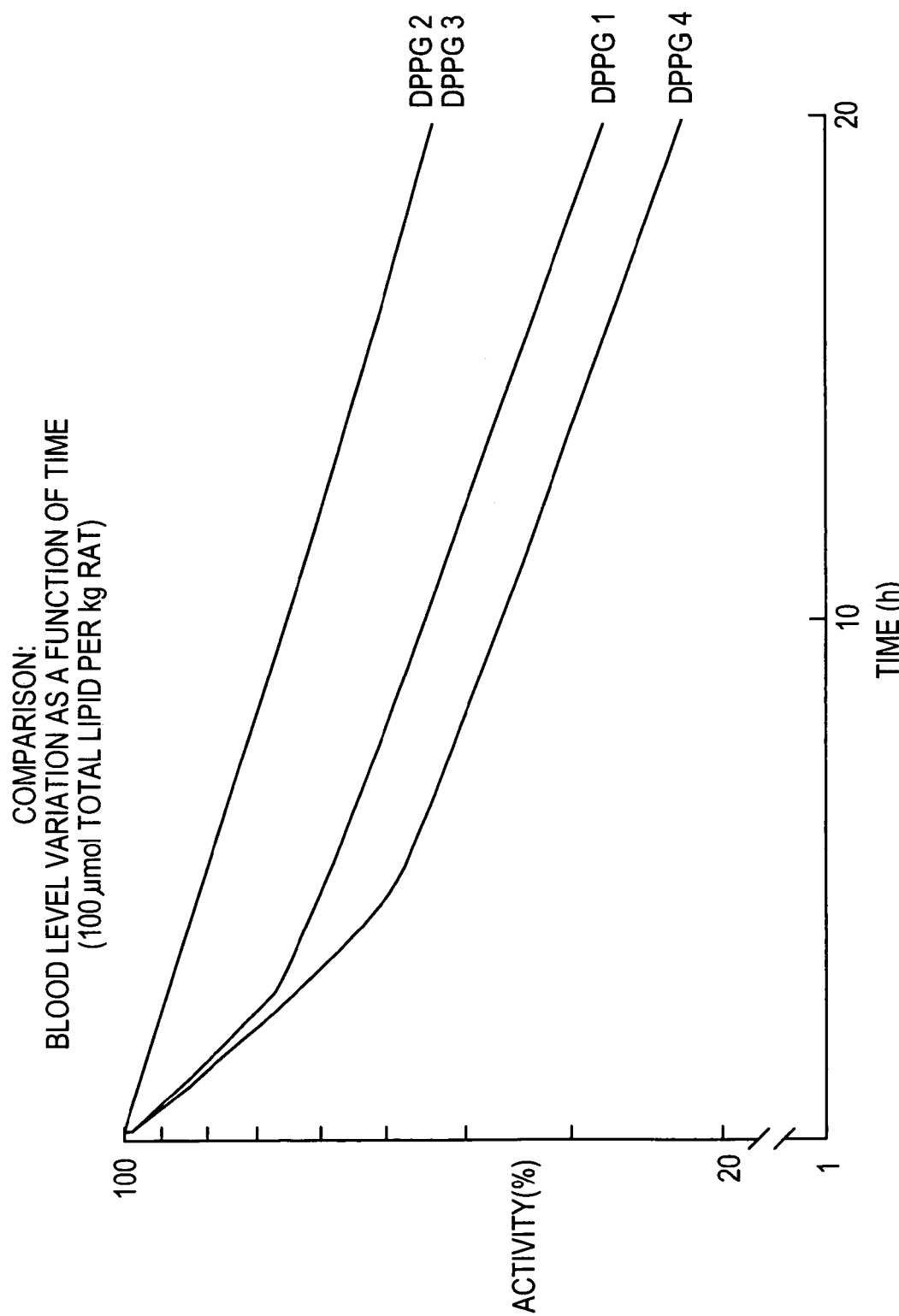
FIG. 3 shows how the blood levels of different liposomes of the invention vary as a function of time.

In FIG. 2, the liposome uptake by the spleen and the liver is depicted as uptake per gram of the organ. For n=4, the spleen is seen to have a liposome concentration which is about 9 times higher than that of the liver; for n=1, the enrichment factor equals 4. In the last column, FIGS. 1 and 2 show the effect which the size of the liposomes has. For LUVs with a diameter of 190 nm, liposome enrichment is even more in favour of the spleen: even when n only equals 2, the enrichment factor equals 24. In practical terms, this means that it is no longer possible to target the liver with these liposomes.

EXAMPLE 4

Preparation of Compounds with the Formula (A)

EXAMPLE 4a

Key Intermediate with the Formula I

The oligoglycerols diglycerol (G$_2$), triglycerol (G$_3$) and tetraglycerol (G$_4$) can be prepared from an easily obtained key intermediate with the formula I, 1.2-isopropylidene-rac-glycero-3.1-rac-glycero-3-allylether, (see model A).

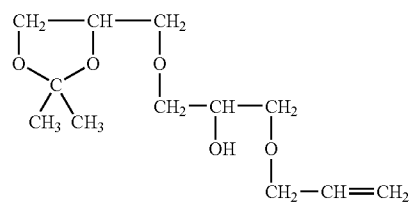

Model A: Oligoglycerols from Formula I

The intermediate product described by formula I can be obtained in large quantities from commercial allyl glydidyl ether by NaOH-catalyzed ring opening with 1.2-isopropylidene-rac-glycerol, which is likewise available in the chemicals trade:

Epoxide Opening with Alcohols (General Example)

Production of the key intermediate with the formula I:
1.2-isopropylidene-rac-$G_1$-3.1-0.0-3-0-allyl-rac-$G_2$

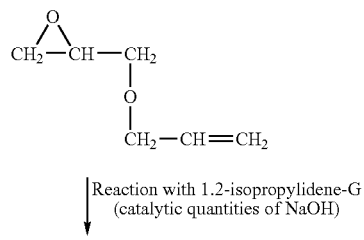

Reaction with 1.2-isopropylidene-G
(catalytic quantities of NaOH)

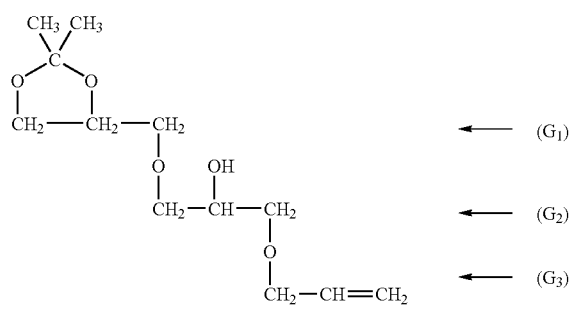

A catalytic quantity of NaOH (MW 40.00; 0.6 mol-24 g) is added to 1.2-isopropylidene-rac-glycerol (MW 132.16; 16 mol-2115 g), which is rendered a solution by stirring and heating to 80° C. At 80° C., allyl glycidyl ether (MW 114.14; 6 mol-685 g) is added dropwise over a period of 2 hours, and the reaction mixture stirred for another 2 hours at 80° C. By this point in time the epoxide ($R_f$ in ether=0.8) has reacted completely to form the $G_3$ constituent ($R_f$ in ether=0.6) The excess isopropylidene-rac-glycerol has an $R_f$ of 0.65 in ether and is removed from the reaction mixture at 75° C./10 mbar. The residue has 1 l diisopropyl ether added to it and is extracted twice with 1 l NaCl (1% solution in $H_2O$) in each case. The organic phase is rotated in an evaporator and distilled ($Kpi_{10}$-1 mbar 125° C.).

The yield of the pure product 1.2-isopropylidene-rac-$G_1$-3.10.0-3-0-allyl-rac-$G_2$ (MW 246.30) is 1025 g (ca. 70%).

Instead of 1.2-isopropylidene-rac-glycerol, it is possible to react other primary alcohols and also allyl alcohol and benzyl alcohol under the given conditions. In the same way, it is also possible to use other epoxides.

The intermediate product with the formula I can also be obtained from 1.2-isopropylidene-rac-glycero-3-glycidyl ether by means of NaOH-catalyzed ring opening with allyl alcohol. In this case, 1.2-isopropylidene-rac-glycero-3 glycidyl ether must first be made from allyl glycerol.

EXAMPLE 4b

Alkylation of Primary or Secondary Hydroxyl Groups (General Example)

Preparation of a Key Intermediate:
1.2-isopropylidene-rac-$G_1$-3.1-0.0-2-0-benzyl-3-0-allyl-rac-$G_2$

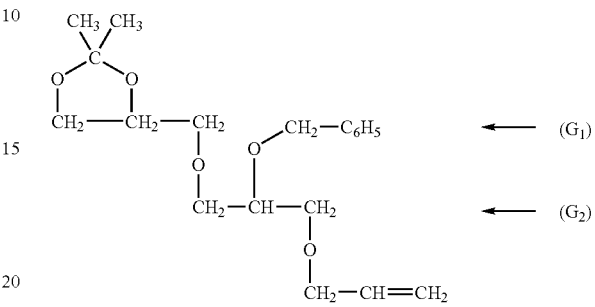

The key intermediate, 1.2-isopropylidene-rac-$G_1$-3.1-rac-$G_2$-0-allyl ether (MW 246.30; 0.5 mol-123 g) is dissolved in 500 ml tetrahydrofuran, has benzyl chloride (0.6 mol-76 g) added to it and is reflux-boiled. K-tert. butylate (0.7 mol-79 g) dissolved in 500 ml tetrahydrofuran is added dropwise. The reaction is completed after 30 minutes of reflux-boiling (TLC check—$R_f$ in ethyl ether educt, $R_f$=0.1; product, $R_f$=0.4). The reaction mixture has 1 l diisopropyl ether and 1 l 1% NaCl solution added to it, is shaken, and the upper phase rotated in an evaporator. The product can either be used directly, or recovered in pure form in approximately 90% yield by means of chromatography on silica gel.

Empirical formula $C_{19}H_{28}O_5$ (MW 336.42) calculated: C, 67.83; H, 8.39; O, 23.79. measured: C, 67.78; H, 8.34; O, -

Instead of benzyl chloride, use can also be made of benzyl bromide, allyl chloride or allyl bromide, or of the halogenides or mesylates of primary alcohols. The products of the reaction between primary or secondary hydroxyl groups and alkyl mesylates, in particular, lead to high yields (>90%) of the desired target compounds.

EXAMPLE 4c

Synthesis Sequence 0-aAllyl ether→0-propenyl ether→alcohol (General Example)

Preparation of 2-0-benzyl-rac-$G_1$-1.3-0.0-1.2-isopropylidene-rac-$G_2$

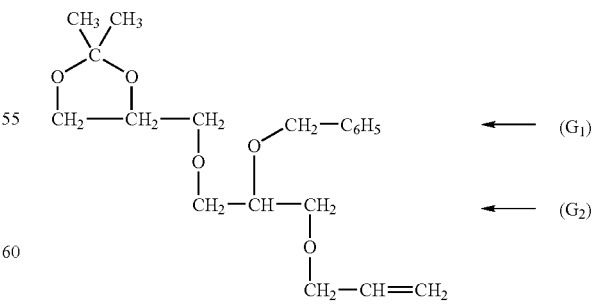

1) K-tert. butylate in dimethyl-formamide
2) HCl 7 $H_2O$ in 1-propanol

-continued

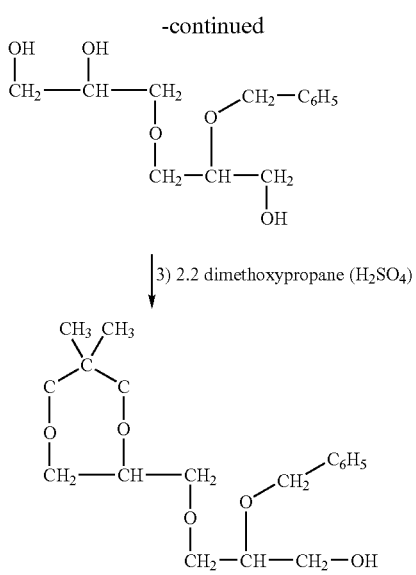

Rearrangement 1.2-isopropylidene-rac-$G_1$-3.1-0.0-2-0-benzyl-3-0-allyl-rac-$G_2$ (0.5 mol-168 g) is dissolved in 500 ml DMF, to which k-tert. butylate (0.7 mol-79 g) is then added. The reaction mixture is heated to 110 to 115° C. with continuous stirring, left for 15 minutes at this temperature and then cooled to 20° C. Following the addition of 500 ml diisopropyl ether and 500 ml 1% NaCl, the upper, diisopropyl ether phase is removed and the solvent eliminated under vacuum (TLC check—$R_f$ in hexane/diisopropyl ether (1:1): educt, $R_f$=0.2; product, $R_f$=0.4).

Cleavage of the Propenyl Protective Group

The residue from the above reaction, approximately 168 g, is dissolved in 500 ml methanol and, following addition of 50 ml 1 M HCl, is reflux-boiled. The reaction is complete after 60 minutes (TLC check in hexane/diisopropyl ether (1:1): educt, $R_f$=0.4; product, $R_f$=0). The yield of rac-$G_1$-3.1-rac-G2-2-0-benzyl ether is >90%. Under the acidic conditions prevailing during propenyl cleavage, the isopropylidene protective group is likewise removed. If necessary, it can be reintroduced in the 1.2 position.

Introduction of the Isopropylidene Protective Group

The residue from the above reaction (approx. 0.5 mol) is dissolved in 300 ml THF to which, in succession, 2.2-dimethoxypropane (0.5 mol-52 g) and 0.2 g $H_2SO_4$ in 10 ml THF are added, and then stirred for 2 hours at 25° C. The reaction mixture is neutralized with saturated $Na_2CO_3$ solution, the precipitate removed under suction and the filtrate rotated with xylol under vacuum to free it of water. The product is purified chromatographically on silica gel 60 (Merck, grain size 0.2-0.5 mm) ($R_f$ in diethyl ether: educt, $R_f$=0.0; product, $R_f$=0.4). One obtains 121 g of the important intermediate needed for the preparation of phosphatidyldiglycerols ($G_2$ parent substance).

$G_2$ Parent System: 2-0-benzyl-rac-$G_1$-1.3-0.0-1.2-isopropylidene-rac-$G_2$ (yield 82%).

Empirical formula: $C_{16}H_{24}O_5$ (MW 296.36) calculated: C, 64.85; H, 8.16; O, 26.99. measured: C, 64.82; H, 8.14; O, -

Intermediates which have higher proportions of oligoglycerol and are likewise needed for the production of phosphatidyl oligoglycerols can be prepared analogously. Some analytical findings pertaining to key intermediates are summarized below:

$G_3$ Parent System: 2-0-benzyl-rac-$G_1$-1.3-0.0-2-0-benzyl-rac-$G_2$-1.3-0.0-1.2-isoproplydene-rac-$G_3$ Empirical formula: $C_2H_{36}O_7$ (MW 460.56) calculated: C, 67.81; H, 7.88; O, 24.32. measured: C, 67.75; H, 7.85; O, -

$G_4$ Parent System:
2-0-benzyl-rac-$G_1$-[1.3-0.0-2-0-benzyl-G]$_2$-1.3-0.0-1.2-isopropylidene-rac-$G_4$ Empirical formula: $C_{36}H_{48}O_9$ (MW 624.77) calculated: C, 69.21; H, 7.74; O, 23.05 measured: C, 69.17; H, 7.69; O, -

$G_6$ Parent System:
2-0-benzyl-rac-$G_1$-[1.3-0.0-2-0-benzyl-rac-G]$_4$-1.3-0.0-1.2-isopropylidene-rac-$G_6$ Empirical formula: $C_{56}H_{72}O_{13}$ (MW 953.172) calculated: C, 70.57; H, 7.61; O, 21.82 measured: C, 70.56; H, 7.54; O, -

$G_8$ Parent System:
2-0-benzyl-rac-$G_1$-[1.3-0.0-2-0-benzyl-rac-G]$_6$-1.3-0.0-1.2-isopropylidene-rac-$G_8$ Empirical formula: $C_{76}H_{96}O_{17}$ (MW 1281.58) calculated: C, 71.23; H, 7.55; O, 21.22 measured: C, 71.15; H, 7.53; O, -

EXAMPLE 4d

Substances which Bear the Tetrahydropyranyl Protective Group (Instead of Benzyl)

(Preparation of Phosphatidyl Oligoglycerols Which Contain Unsaturated Fatty Acids)

For this variant, 1.2-isopropylidene-rac-glycero-3-0-allyl ether is prepared and epoxidized as described by H. Eibl and P. Woolley (Chem. Phys. Lipids 41 (1986) 53-63).

Epoxidation (General Example)

1.2-isopropylidene-rac-glycero-3-0-allyl ether (MW 172.22; 1 mol-172 g) is dissolved in 1 l $CH_2Cl_2$. 3-chloroperoxybenzoic acid (1.1 mol) is added portion-wise and the reaction mixture stirred for 6 hours at 25-30° C. The educt ($R_f$ 0.5 in diethyl ether/pentane 1:1) is by then transformed completely into the desired product ($R_f$ 0.2 in the above system). After removing the precipitate by suction filtration, 100 g $Na_2CO_3$ is added to the filtrate and the mixture stirred for another 3 hours at 20° C. The precipitate is removed and the solvent eliminated under vacuum. The yield of epoxide (MW 188.22) is 170 g (90%). As described under "epoxide opening with alcohols" (Example 4a), the epoxide is now converted with benzyl alcohol into 1-0-benzyl-rac-$G_1$-3.1-0.0-2.3-isopropylidene-rac-$G_2$ and the free —OH groups converted with 3.4-dihydro-2H-pyran into the tetrahydropyran derivative.

Introduction of the Tetrahydropyran Protective Group (General Example)

1-0-benzyl-rac-$G_1$-3.1-0.0-2.3-isopropylidene-rac-$G_2$ (MW 296.36; 1 mol-296 g) is dissolved in 1 l THF, to which 1.4 mol 3.4-dihydro-2H-pyran and 0.1 mol toluene sulfonic acid are added. The reaction is complete after 1 hour (educt, $R_f$ 0.65; product, $R_f$ 0.90 in diethyl ether). 1 1 0.2 mol $Na_2CO_3$ solution and 1 l diisopropyl ether are added, and the mixture shaken thoroughly in a separating funnel. The upper phase is rotated in an evaporator and the product converted by means of hydrogenolysis with $H_2$ in the presence of a PD/C catalyst (5% Pd based on the alcohols) into the $G_2$ constituent with free hydroxyl group.

$G_2$ Parent System: 2-0-tetrahydropyranyl-rac-$G_1$-1.3-0.0-1.2-isopropylidene-rac-$G_2$ (Yield 80% Expressed in Terms of the Epoxide)

Empirical formula: $C_{14}H_{27}O_6$ (MW 291.36) calculated: C, 57.71; H. 9.34; O, 32.95 measured: C, 57.59; H. 9.29; O, -

Compounds with other parent systems can be converted into THP-protected structures in the same way. For example, the 3-0-allyl ether of example 4a can be converted to an epoxide and opened with allyl alcohol. Again, a 3-0-allyl ether is formed, which is epoxidized and opened with benzyl alcohol to form the product below, which, through introduction of 3 THP protective groups and catalytic hydrogenolysis, can be converted to an intermediate with the $G_4$ parent system.

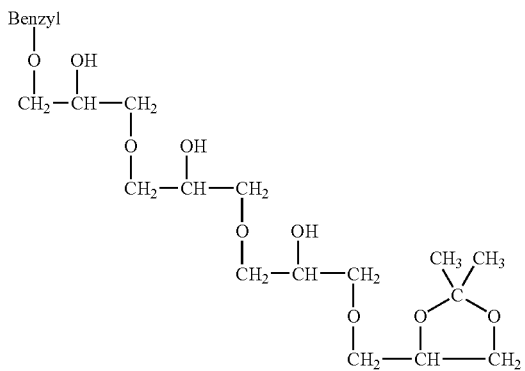

$G_4$ Parent System:
2-O-THP-rac-$G_1$[1.3-0.O-2-0-THP-rac-G]$_2$-1.3-0.0-1.2-isopropylidene-rac -$G_4$ Empirical formula: $C_{30}H_{45}O_2$ (MW 607.75) calculated: C, 59.29; H, 9.12; O, 31.59 measured: C, 59.24; H, 9.08; O, -

EXAMPLE 4e

Further Processing of the Intermediate with the Formula I $G_2$ Parent System (Racemic)

From formula I, a key intermediate for the preparation of the $G_2$ parent system is obtained (see model B). To this end, the secondary —OH function in formula I is alkylated, benzylated, or protected with tetrahydropyran.

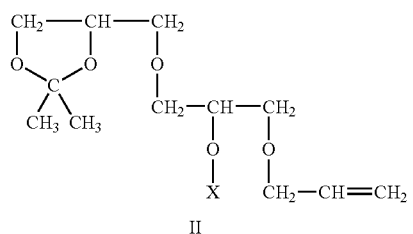

Formula I

Model B: Key Intermediate for Preparing the $G_2$ Parent System:

X=saturated or unsaturated alkyl, benzyl or THP

Alkyl-$G_2$ Compounds 1) 2-0-alkyl-rac-$G_1$-1.3-0.0-rac-$G_2$

The intermediate compound of formula II in which X=alkyl is freed of the protective groups. The following compounds were isolated:

| | | |
|---|---|---|
| 2-O-ethyl-$G_2$: | $C_8H_{18}O_5$ | (194.23) |
| 2-O-hexyl-$G_2$: | $C_{12}H_{26}O_5$ | (250.33) |
| 2-O-undecenyl-$G_2$: | $C_{17}H_{34}O_5$ | (318.45) |
| 2-O-dodecyl-$G_2$: | $C_{18}H_{38}O_5$ | (334.49) |
| 2-O-octadecyl-$G_2$: | $C_{24}H_{50}O_5$ | (418.65) |
| 2-O-erucyl-$G_2$: | $C_{28}H_{56}O_5$ | (472.75) |

2) 1-0-alkyl-rac-$G_1$-3.1-0.0-rac-$G_2$

In the intermediate compound of formula If in which X=benzyl, allyl is removed from the 1-position and the corresponding alkyl chain incorporated in the 1-position. Following removal of the protective groups, the following compounds were obtained:

| | | |
|---|---|---|
| 1-O-methyl-$G_2$: | $C_7H_{16}O_5$ | (180.20) |
| 1-O-propyl-$G_2$: | $C_9H_{20}O_5$ | (208.25) |
| 1-O-nonyl-$G_2$: | $C_{15}H_{32}O_5$ | (292.41) |
| 1-O-undecyl-$G_2$: | $C_{17}H_{36}O_5$ | (320.47) |
| 1-O-dodecyl-$G_2$: | $C_{18}H_{38}O_5$ | (334.49) |
| 1-O-octadecyl-$G_2$: | $C_{24}H_{50}O_5$ | (418.65) |

Unsaturated 1-O-alkyl diglycerols can also be obtained directly by way of epoxide opening of 1.2-isopropylidene-glycero-glycidyl ether (Model D, formula IV) with alcohols, eg, 1-O-Undecenyl-$G_2$: $C_{17}H_{34}O_5$ (318.45)

However, this path is only suitable for shorter-chain alcohols, since the yields for long-chain alcohols such as oleyl alcohol are low. To prepare 1-oleyl-$G_2$, therefore, a synthetic pathway via 2-O-THP-glycero-1.3.0.0-(1.2-isopropylidene)-glycerol is preferred (model D, formula V)

1-O-Oleyl-$G_2$: $C_{24}H_{48}O_5$ (416.64)

Intermediates for the Synthesis of Phospholipids which Contain Diglycerols in the Polar Area Compounds with good protective groups for these syntheses contain a 2-O-benzyl ether or a 2-O-tetrahydropyranyl ether group in $G_1$.

---

1) 2-O-benyzl-rac-$G_1$-1.3-0.0-(1.2-isopropylidene)-rac-$G_2$:

$C_{16}H_{24}O_5$          (296.36)

---

The compound with the formula III is obtained by alkaline allyl/propyl rearrangement, benzylation of the secondary —OH group and subsequent acidic cleavage of the propenyl protective group.

Formula I

1) Rearrangement allyl/propenyl
2) Benzylation
3) Acidic cleavage

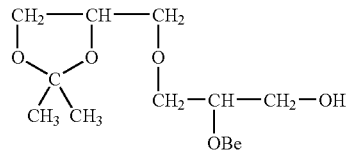

Model C: Starting Product for Phosphatidyl Diglycerols with Saturated Fatty Acid Residues.

---

2) 2-O-tetrahydropyranyl-rac-$G_1$-1.3-0.0-(1.2-isopropylidene)-rac-$G_2$:

$C_{14}G_{27}O_6$          (291.36)

---

The compound with the formula V is made from allyl glycerol. The intermediate IV is obtained by way of addition of isopropylidene followed by epoxidation. After opening the epoxide with benzyl alcohol, the THP protective group is introduced and the benzyl group removed.

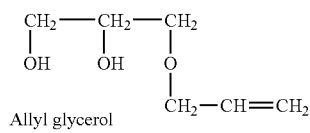
Allyl glycerol

1) H$^+$; 2.2 dimethoxy propane
2) Epoxidation

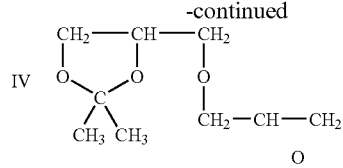
IV

3) Opening with benzyl alcohol

4) H$^+$;

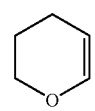

5) H$_2$; Pd/C

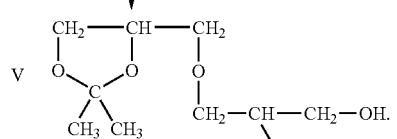
V

Model D: Starting Product for Phosphatidyl Diglycerols with Unsaturated Fatty Acid Residues $G_3$ Parent System (Racemic)

From the key intermediate with the formula II it is possible, with inclusion of the allyl group, to develop triglycerols. Following epoxidation, various intermediates and end products of pharmaceutical interest can be made from the epoxide.

Intermediate II

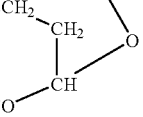

Epoxidation

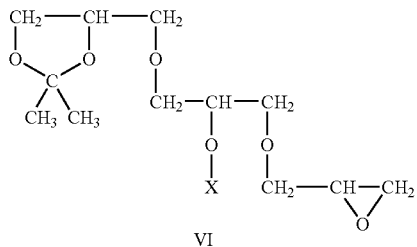
VI

Model E: Starting Products for Making $G_3$ Parent Systems.

Triglycerols can be prepared from the key intermediate with the formula VI; the intermediate is also used for making $G_4$ parent systems. In formula VI, X stands for hydrogen, a saturated alkyl, a benzyl or a THP residue.

Alkyl-$G_3$ Compounds 1) 1-O-alkyl-rac-$G_1$-1.3-0.0-rac-$G_2$-1.3-0.0-rac-$G_3$ The epoxide with the formula VI (X=H) is opened directly with alcohols and, after the isopropylidene protective group has been split off, results in the following compounds:

| | | |
|---|---|---|
| 1-O-ethyl-$G_3$: | $C_{11}H_{24}O_7$ | (268.30) |
| 1-O-hexyl-$G_3$: | $C_{15}H_{32}O_7$ | (324.41) |
| 1-O-nonyl-$G_3$: | $C_{18}H_{38}O_7$ | (366.491) |
| 1-O-undecenyl-$G_3$: | $C_{20}H_{40}O_7$ | (392.53) |
| 1-O-dodecyl-$G_3$: | $C_{21}H_{44}O_7$ | (408.57) |

For longer-chain alcohols, direct opening results in poor yields. For this reason, the oleyl and erucyl compounds of $G_3$ were prepared by opening of V (X=THP) with benzyl, THP-protection of the secondary hydroxyl groups formed, catalytic debenzylation, alkylation in the 1 position and removal of the protective groups.

| | | |
|---|---|---|
| 1-O-oleyl-$G_3$: | $C_{27}H_{54}O_7$ | (490.72) |
| 1-O-erucyl-$G_3$: | $C_{31}H_{62}O_7$ | (456.82) |

2) 2-O-alkyl-rac-$G_1$-1.3-0.0-rac-$G_2$-1.3-0.0-rac-$G_3$

The epoxide of formula VI (X=benzyl or THP) is opened with allyl alcohol and alkylated in the 2 position. The protective groups are removed in the usual way. For the preparation of the unsaturated 2-0-alkyl compounds, rearrangement of the allyl protective groups must precede alkylation. In addition, only the THP protective group and not benzyl can be used in $G_2$ here. The following compounds were prepared:

| | | |
|---|---|---|
| 2-O-methyl-$G_3$: | $C_{10}H_{22}O_7$ | (111.99) |
| 2-O-propyl-$G_3$: | $C_{12}H_{26}O_7$ | (282.33) |
| 2-O-nonyl-$G_3$: | $C_{18}H_{38}O_7$ | (366.49) |
| 2-O-undecenyl-$G_3$: | $C_{20}H_{40}O_7$ | (392.53) |
| 2-O-dodecyl-$G_3$: | $C_{21}H_{44}O_7$ | (408.57) |
| 2-O-hexadecyl-$G_3$: | $C_{25}H_{52}O_7$ | (464.68) |
| 2-O-oleyl-$G_3$: | $C_{27}H_{54}O_7$ | (490.72) |
| 2-O-erucyl-$G_3$: | $C_{31}H_{62}O_7$ | (546.82) |

Intermediates for the Synthesis of Phospholipids Which Contain Trigylcerides in the Polar Area Benzyl and tetrahydropyranyl (THP) residues are convenient protective groups for synthesizing phospholipids which have $G_3$ residues in the polar area. Benzyl residues are readily removed under mild conditions, provided that only saturated fatty acids are used. THP residues are of particular interest because they can be removed in a single step together with isopropyl protective groups.

| 1) 2-O-benyzl-rac-$G_1$-1.3-0.0-(2-O-benzyl)-rac-$G_2$-1.3-0.0-(1.2-isopropylidene)-rac-$G_3$ | |
|---|---|
| $C_{26}H_{36}O_7$ | (460.56) |

This compound is obtained from the key intermediate VI (X=benzyl) by opening with allyl alcohol, benzylation of the 2 position and cleavage of the allyl protective group. In the text, the compound is referred to as formula VII.

| 2) 2-O-THP-rac-$G_1$-1.3-0.0-(2-O-THP)-rac-$G_2$-1.3-0.0-(1.2-isopropylidene)-rac-$G_3$: | |
|---|---|
| $C_{22}H_{41}O_9$ | (449.56) |

To prepare unsaturated $G_3$-phospholipids, the residue X=THP is used in VI. The epoxide VI is opened with benzyl alcohol, the secondary hydroxyl group thus exposed protected with THP, and the benzyl residue removed catalytically with $H_2$/Pt. The compound made in this way is referred to in the text as formula VIII.

Additional Remarks

In the description so far we have not made use of the fact that in formula VI for X=saturated alkyl, compounds of the following structure can readily be prepared: 1-O-alkyl-rac-$G_1$-3.1-0.0-(2-0-alkyl)-rac-$G_2$-3.1-rac-$G_3$. The representatives of these new structures were made by opening the epoxide VI (X=hexadecyl) with $CH_3OH$ or undecenyl alcohol and splitting off the isopropylidene protective group.

| 1-O-methyl-rac-$G_1$-3.1-O.O-(2.O-hexadecyl)-rac-$G_2$-3.1-rac-$G_3$: | |
|---|---|
| $C_{26}H_{54}O_7$ | (478.71) |
| 1-O-Undecenyl-rac-$G_1$-3.1-O.O-(2-O-hexadecyl)-rac-$G_2$-3.1-O.O-rac-$G_3$: | |
| $C_{36}H_{72}O_7$ | (616.958) |

$G_4$ Parent System (Racemic)

$G_4$ parent systems can be prepared from the key intermediate with the formula IX.

Intermediate VI

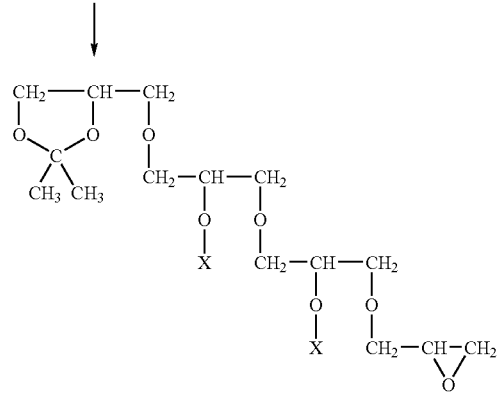

X = H, saturated alkyl, benzyl or THP
1) Opening with allyl alcohol
2) X = H: epoxidation
   X = Be: benzylation of 2-OH, followed by epoxidation
   X = THP: Introduction of THP in 2-OH, followed by epoxidation Model F: Starting Products for the Preparation of $G_4$ Parent Systems.

Tetraglycerols can be made from the key intermediate with the formula IX. They can also be used to prepare pentaglycerols.

Oligoglycerols with two or more alkyl residues can be made from the intermediates, too. Suitable starting compounds here are molecules with the formula IX, in which X is a saturated alkyl residue.

Alkyl-$G_4$ Compounds 1) 1-O-alkyl-rac-$G_1$-1.3-0.0-rac-$G_2$-1.3-0.0-rac-$G_3$-1.3-0.0-rac-$G_4$ The epoxide of formula IX, X=H, is opened directly with alcohols. After the isopropylidene protective group has been split off, the following substances are obtained:

| | | |
|---|---|---|
| 1-0-ethyl-$G_4$: | $C_{14}H_{30}O_9$ | (342.38) |
| 1-0-hexyl-$G_4$: | $C_{18}H_{38}O_9$ | (398.49) |
| 1-0-undecyl-$G_4$: | $C_{19}H_{40}O_9$ | (412.52) |
| 1-0-undecenyl-$G_4$: | $C_{19}H_{38}O_9$ | (410.50) |
| 1-0-dodecyl-$G_4$: | $C_{20}H_{42}O_9$ | (426.54) |

This path is only suitable for shorter-chain alcohols, since the yields are much lower with long-chain alcohols.

For long-chain, saturated alcohols it is therefore necessary, as with $G_2$ and $G_3$, to select a synthetic pathway via the key intermediate with X=benzyl. One opens with allyl alcohol, benzylates the thus exposed 2-OH group, removes the allyl group in the 1 position and alkylates the 1 position. After removing the protective groups one obtains:

| | | |
|---|---|---|
| 1-0-hexadecyl-$G_4$: | $C_{24}H_{50}O_9$ | (482.99) |
| 1-0-octadecyl-$G_4$: | $C_{26}H_{54}O_9$ | (510.70) |
| 1-0-behenyl-$G_4$: | $C_{30}H_{62}O_9$ | (566.81) |

2. 2-O-alkyl-rac-$G_1$-1.3-0.0-rac-$G_2$-1.3-0.0-rac-$G_3$-1.2-0.0-rac-$G_4$

The key intermediate with the formula IX is opened with allyl alcohol, and the thus-exposed 2 position alkylated. After removal of the protective groups one obtains:

| | | |
|---|---|---|
| 2-0-propyl-$G_4$: | $C_5H_{32}O_9$ | (356.41) |
| 2-0-hexyl-$G_4$: | $C_{18}H_{38}O_9$ | (398.49) |
| 2-0-nonyl-$G_4$: | $C_{21}H_{44}O_9$ | (440.57) |
| 2-0-undenyl-$G_4$: | $C_{19}H_{38}O_9$ | (410.50) |
| 2-0-dodecyl-$G_4$: | $C_{20}H_{42}O_9$ | (426.54) |
| 2-0-hexadecyl-$G_4$: | $C_{24}H_{40}O_9$ | (483.99) |
| 2-0-octadecyl-$G_4$: | $C_{26}H_{54}O_9$ | (510.70) |
| 2-0-oleyl-$G_4$: | $C_{26}H_{52}O_9$ | (508.69) |
| 2-0-erucyl-$G_4$: | $C_{30}H_{60}O_9$ | (564.80) |

Intermediates for the Synthesis of Phospholipids which have Tetraglycerols in the Polar Area.

As with the synthesis of $G_2$ and $G_3$ compounds, benzyl and tetrahydropyran ether are suitable protective groups for these syntheses.

1) 2-O-benzyl-rac-$G_1$-1.3-0.0-(2-0-benzyl)-rac-$G_2$-1.3-0.0-(2-0-benzyl)-rac-$G_3$-1.3-0.0-(1.2-isopropylidene)-rac-$G_4$:

| | |
|---|---|
| $C_{36}H_{48}O_9$ | (624.77) |

The important intermediate for the synthesis of phospholipids with $G_4$ residues in the polar area is made from formula IX, X=benzyl by opening the epoxide with allyl alcohol, benzylating the thus exposed 2-OH group and removing allyl. The compound is referred to as formula X in the text.

2. 2-0-THP-rac-$G_1$-1.3-0.0-(2-0-THP)-rac-$G_2$-1.3-0.0-(2-0-THP)-rac-$G_3$-1.3-0.0-(1.2-isopropylidene)-rac-$G_4$:

| | |
|---|---|
| $C_{30}H_{45}O$ | (607.75) |

To make this compound, which is suitable for obtaining unsaturated phospholipids with $G_4$ parent systems in the polar area, one proceeds analogously as for the preparation of the $G_3$ compound. One opens the epoxide VII, X=THP with benzyl alcohol, protects the thus exposed 2-OH group with THP, and removes benzyl with $H_2$ (Pd/C catalysis.). The compound is referred to in the text as formula XI.

Intermediates for the Synthesis of Phospholipids which Contain Oligoglycerols in the Polar Area and Permit an sn-1 Linkage to the Phosphate (Natural Configuration)

In the preparation of compounds suitable for incorporation in the polar area of phospholipids (formula III and V for $G_2$, formula VII and VIII for $G_3$, formula X and XI for $G_4$), no attention was paid so far to the fact that in natural phosphatidylglycerol, ie, in 1.2-diacyl-sn-glycero-3-phospho-sn-1-glycerol, the link between phosphate and the non-acylated glycerol is an sn-1 linkage. Since the liposome components, as carriers of medicinal products, should be used in the most natural configuration possible, synthetic pathways were developed which also permit an sn-1 configuration of the polar oligoglycerol (model G).

sn-1-$G_1$-$G_2$ Linkage

The stereospecific linkage can be obtained using methods analogous to those described in the literature (DE 31 30 867 A1; H. Eibl, Chem. Phys. Lipids 28 (1981) 1-5; H. Eibl et al., Chem. Phys. Lipids 41 (1986) 53-63; H. Eibl et al., Chem. Phys. Lipids 47 (1988) 47-53).

The starting product for this linkage is 2-0-benzyl-3-0-allyl-sn-glycerol, which, following epoxidation, is hydrolysed to the diol. Following reaction with $H^+$/2.2-dimethoxypropane, 2-0-Be-sn-$G_1$-3. 1-0.0-(1.2-isopropylidene)-rac-$G_2$ is obtained, a molecule with the formula XII, which permits an sn-1 linkage to the phosphate group in phospholipids and corresponds to the racemate of formula III.

sn-1-$G_1$-$G_2$-$G_3$ Linkage

The starting product for this linkage is again 2-0-benzyl-3-0-allyl-sn-glycerol. Protection of the sn-1 position with THP is followed by epoxidation, and then the epoxide ring opened with 1.2-isopropylidene glycerol. The thus-exposed —OH function in $G_2$ is benzylated, and the THP protective group removed. One obtains a molecule with the formula XIII, which permits an sn-1 linkage to the phosphate group in phospholipids. The molecule XIII corresponds to the racemate of formula VI.

sn-1-$G_1$-$G_2$-$G_3$-$G_4$ Linkage

The starting product is again 2-0-benzyl-3-0-allyl-sn-glycerol, in order to ensure the sn-1 linkage. Incorporation of the THP protective group is followed by epoxidation, and the epoxide then opened with allyl alcohol. Following epoxidation of the intermediate, the epoxide is opened with isopropylidene glycerol, the two exposed —OH groups benzylated, and THP removed. One obtains XIV, which permits an sn-1 linkage to the phosphate and corresponds to the racemate of formula X.

If desired, compounds with an sn-3-$G_1$-$G_2$, sn-3-$G_1$-$G_2$-$G_3$ or sn-3-$G_1$-$G_2$-$G_3$-$G_4$ linkage with the phosphate can be made analogously. In this case, the same sequence of reactions is required, but instead of 2-0-benzyl-2-0-allyl-sn-glycerol, use is made of the enantiomeric 2-0-benzyl-1-0-allyl-sn-glycerol.

sn-1-$G_1$-$G_2$ linkage

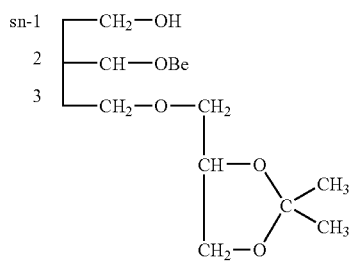

XII sn-1-$G_1$-$G_2$-$G_3$ linkage

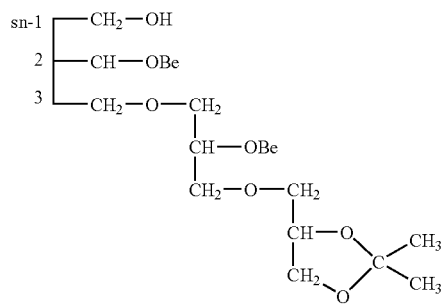

XIII sn-1-$G_1$-$G_2$-$G_3$-$G_4$ linkage

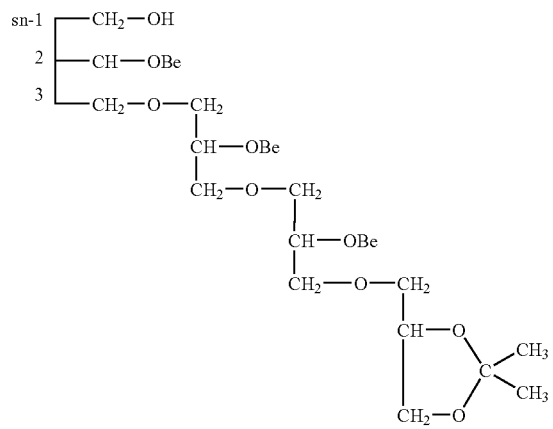

XIV

Model G: Phospholipid Constituents Which Permit an sn-1-$G_x$ Linkage (x=2-4). Starting Product is 2-O-benzyl-3-O-allyl-sn-glycerol.

EXAMPLE 4f

Intermediates which Contain Sugar Alcohols
(General Examples)

Important intermediates here are, in particular, such sugar alcohols as are obtainable at a reasonable price or can be made from these by means of simple reactions (see enclosed table). Of special interest are D-mannitol as open form of inositol, xylitol, which, when the middle carbon atom is phophorylated, shows no optical activity and which is readily obtained as 1.2; 4.5-diisopropylidene xylitol, and meso-erythritol. The protective groups chiefly employed here are isopropylidene, trityl in combination with benzyl, or allyl. Tetrahydropyranyl is also of some importance as protective group. Some alternatives will now be described which serve as examples.

1.2;4.5-diisopropylidene-xylitol (General Example for Introduction of the Isopropylidene Protective Group)

Xylitol (1.0 mol-152 g) is slurried with 500 ml 2-propanol, and mixed with dimethoxypropane (3.0 mol-312 g). Following addition of 6 g $H_2SO_4$ in 100 ml 2-propanol, the mixture is heated to 50° C. After 30 minutes everything has dissolved. Sufficient concentrated ammonia is added to adjust the reaction mixture to a pH of about 8. The solvent is removed in a rotary evaporator, and the residue taken up in hexane and cooled to −20° C. White crystals precipitate, which are sucked up and used for the phosphorylation.

Empirical formula: $C_{11}H_{19}O_5$ (MW 231.27) calculated: C, 57.13; H, 8.28; O, 34.59 measured: C, 57.01; H, 8.27; O, -

Structural Formulae of Some Sugar Alcohols:

$C_4H_{10}O_4$

| meso-Erythritol | D-Threitol | L-Threitol |
|---|---|---|
| $CH_2OH$ | $CH_2OH$ | $CH_2OH$ |
| H———OH | HO———H | H———OH |
| H———OH | H———OH | HO———H |
| $CH_2OH$ | $CH_2OH$ | $CH_2OH$ |

$C_5H_{12}O_5$

| Adonite (Ribitol) | D(+)-Arabitol | L(−)-Arabitol | Xylitol |
|---|---|---|---|
| $CH_2OH$ | $CH_2OH$ | $CH_2OH$ | $CH_2OH$ |
| H———OH | HO———H | H———OH | H———OH |
| H———OH | H———OH | HO———H | HO———H |
| H———OH | H———OH | HO———H | H———OH |
| $CH_2OH$ | $CH_2OH$ | $CH_2OH$ | $CH_2OH$ |

$C_6H_{14}O_6$

|  Dulcite (Galactit.) | D-Mannitol | D-Sorbitol |
|---|---|---|
| CH$_2$OH | CH$_2$OH | CH$_2$OH |
| H—OH | HO—H | H—OH |
| HO—H | HO—H | HO—H |
| HO—H | H—OH | H—OH |
| H—OH | H—OH | H—OH |
| CH$_2$OH | CH$_2$OH | CH$_2$OH |

1.2;3.4-diisopropylidene-5-benzyl-D-mannitol
(General Example for the use of Trityl Protective Groups Combined with Benzyl Protective Groups)

Starting with 1.2;3.4;5.6-triisopropylidene-D-mannitol (MW 302.36), which is prepared analogously to the xylitol derivative, one obtains—by means of carefully splitting off the protective group—a 1.2.3.4-diisopropylidene-D-mannitol yield of about 30%. Triisopropylidene-D-mannitol (1.0 mol-302 g) is dissolved in 600 ml CH$_3$OH, to which 15 (5 g) Amberlyst® and 70 g H$_2$O are then added. The reaction mixture is heated to 50° C., the solution stirred at this temperature for 40 minutes (educt, $R_f$ 0.9; 1.2;3.4-derivative, $R_f$ 0.7; 3.4-derivative, $R_f$ 0.1 in CHCl$_3$/CH$_3$OH 1:1), cooled to 20° C. and filtered to 7.5 ml 25% ammonia in 25 ml 2-propanol (pH~8). Cooling to 4° C. causes the starting product to precipitate, which can thus be recovered (ca. 120 g, ~40%). The filtrate is rotated in an evaporator and purified chromatographically on silica gel 60 (Merck, Darmstadt). One obtains 84 g (~32%) of 1.2;3,4-diisopropylidene-D-mannitol, which is retrieved in crystalline form from hexane.

Empirical formula: $C_{12}H_{22}O_6$ (MW 262.30) calculated: C, 54.95; H, 8.45; O, 36.60 measured: C, 54.89; H, 8.34; O. -

Reaction of 1.2;3.4-diisopropylidene-D-mannitol with Trityl Chloride and Benzyl Chloride (General Example for Tritylation and Subsequent Alkylation)

1.2:3.4-diisopropylidene-D-mannitol (0.2 mol-52 g) is dissolved in 300 ml toluene, mixed with triethylamine (0.30 mol-30 g) and reflux-boiled. Trityl chloride (MW 278.78; mol-64 g) in 200 ml toluene is added dropwise, and the mixture reflux-boiled for another 60 minutes (educt, $R_f$ 0.7; product, $R_f$ 0.90 in CHCl$_3$/CH$_3$OH 10:1). The reaction is then complete. The mixture is cooled to 20° C., precipitated triethylamine hydrochloride filtered off, and the filtrate rotated in an evaporator. The residue is taken up in 400 ml THF, mixed with benzyl chloride (0.3 mol-38 g) and reflux-boiled. K-tert. butylate (0.25 mol-28 g)—dissolved in 200 ml THF—is added dropwise and the reaction mixture left to stand for 1 hour (educt, $R_f$ 0.90; product, $R_f$ 1.00 in CHCl$_3$/CH$_3$OH 10:1). Following addition of 300 ml diisopropyl ether, the reaction mixture is extracted with 600 ml H$_2$O, the upper phase taken off and the solvent removed under vacuum. The residue can be used directly.

Cleavage of the Trityl Protective Group while Retaining the 3.4-Isopropylidene Protective Group (General Example)

The oily residue from the preceding reaction (~0.2 mol) is dissolved in 600 ml acetone/CH$_3$OH 1:1, to which 3 ml H$_2$SO$_4$ are then added. The mixture is stirred at 40° C. for 40 minutes, which results in complete removal of the trityl- and the 1.2-isopropylidene protective groups (educt, $R_f$ 0.95; product, $R_f$ 0.15 in ether). The reaction mixture is adjusted to pH~8, filtered and rotated in an evaporator. The residue is purified chromatographically on silica gel, and crystallized from hexane.

2-0-benyzl-3.4-isopropylidene-D-mannitol

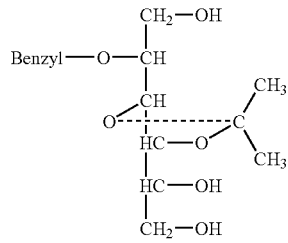

Empirical formula: $C_{16}H_{24}O_6$ (MW 312.36) calculated: C, 61.52; H, 7.74; O, 30.73 Measured: C, 61.44; H, 7.72; O, -

As described for example 4c, the isopropylidene protective group can be reintroduced in the 5.6 position. A key intermediate for the synthesis of phosphatidyl-D-mannitol compounds is obtained, namely 2-0-benzyl-3.4;5.6-diisopropylidene-D-mannitol.

Empirical formula: $C_{19}H_{28}O_6$ (MW 352.42) calculated: C, 64.75; H, 8.01; O, 27.24 measured: C, 64.68; H, 7.94; O, -

Sugar Alcohol Constituents Which are Obtained by Splitting Periodate off a Vicinal Diol and Reducing the Resulting Aldehyde with Sodium Borohydride (General Example)

1.2:3.4-diisopropylidene-D-mannitol (0.2 mol-26 g) is dissolved according to the method of H. Eibl (Chem. Phys. Lipids 28 (1981) 1-5) in 200 ml CH$_3$OH and added to a solution of 0.2 mol sodium metaperiodate in 500 ml water. The temperature should not exceed 30° C. The reaction is complete after 15 minutes. The pH of the reaction mixture is raised to pH=8 with 5 M KOH in water. The precipitated salts are filtered off, and the aldehyde reduced with sodium borohydride (0.25 mol). One obtains a >90% yield of 1.2:3.4-diisopropylidene-D-lyxitol, which is extracted with 600 ml of chloroform. The chloroform phase is rotated in an evaporator and the product crystallized from hexane.

Empirical formula: $C_{11}H_{19}O_5$ (MW 231.27) calculated: C, 57.13; H, 8.28; O, 34.59 measured: C, 57.07; H, 8.21, O, -

By employing the various alternatives—monoisopropylidene cleavage, periodate cleavage from vicinal diols to produce aldehydes which are then reduced with sodium borohydride, and the variation trityl/alkyl—sugar alcohols are obtained that are protected in very different ways. These can be converted by way of acylation or phosphorylation into interesting alkyl, acyl or phosphatidyl compounds.

Preparation of Simple Ester and Ether Derivatives from the Oligoglycerols and Sugar Alcohols Portrayed (General Description)

Methods of esterification and etherification, followed by cleavage of the protective groups, have been described in various publications. The articles listed below include different methods of phosphorylation. These methods can be employed here analogously.

Eibl, H.
Synthesis of glycerophospholipids
Chem. Phys. Lipids 26 (1980) 405-429

Eibl, H.
Phospholipid Synthesis
In: Liposomes: From Physical Structure to Therapeutic Applications (C. G. Knight, editor) Elsevier, Amsterdam (1981) 19-50

Eibl, H. and Kovatchev, S.
Preparation of phospholipids and of their analogues by phospholipase D. In: Methods of Enzymology. Vol. 72. Ed. J. M. Lowenstein, Academic Press, New York (1981) 632-639

Eibl, H.: Phospholipids als funktionelle Bausteine biologischer Membranen Angew. Chemie 96 (1984) 247-262

Eibl, H.: Phospholipids as functional constituents of biomembranes Angew. Chem. Int. Ed. Engl. 23 (1984) 257-271

Eibl, H. Phospholipid synthesis: Oxazapholanes and dioxaphospholanes as intermediates. Proc. Natl. Acad. Sci. USA 75 (1978) 4074-4077

Eibl, H. and Wooley, P.: Synthesis of enantiomerically pure glyceryl esters and ethers. I. Methods employing the precursor 1,2-isopropylidene-sn-glycerol. Chem. Phys. Lipids 41 (1986) 53-63

Eibl. H. and Wooley, P.: Synthesis of enantiomerically pure glyceryl esters and ethers. II. Methods employing the precursor 3,4-isopropylidene-D-mannitol. Chem. Phys. Kipids 47 (1988) 47-53

Eibl. H. and Wooley, P.: A general synthetic method for enantiomerically pure ester and ether lysophospholipids. Chem. Phys. Lipids 47 (1988) 63-68

Wooley, P. and Eibl, H.: Synthesis of enantiomerically pure phospholipids including phosphatidylserine and phosphatidylglycerol. Chem. Phys. Lipids 47 (1988) 55-62

EXAMPLE 4g

Intermediates for the Synthesis of Phospholipids which Contain Sugar Alcohols in the Polar Area As already described, the introduction via oligoglycerols of substances in the polar area of phospholipids has a pronounced effect on the blood circulation if these substances are used as liposome components. The same result can be obtained if, instead of the oligoglycerols, use is made of sugar alcohols, eg, phosphoric acid esters of D-mannitol, D-lyxitol and D-threitol. These compounds can be introduced with suitable protective groups (see model H) into phospholipids in the manner described for oligoglycerols. With the derivatives described, coupling with phospholipids again leads to an sn-1 linkage between the phosphoric acid and the sugar alcohol.

D-Mannitol Derivative 3.4-0.0-dibenzyl-D-mannitol is prepared from 1.2.6.5-diisopropylidene-D-mannitol by benzylating in the 3.4 position and splitting off the isopropylidene protective groups. After introducing the isopropylidene protective group in the 1.2 position, tritylation and benzylation of the exposed —OH group, one obtains, following cleavage of the trityl group, the compound XV, which can be incorporated in the polar area of phospholipids.

D-Lyxitol Derivative 1.2-isopropylidene-3.4-0.0-dibenyzl-D-mannitol (see above) is cleaved with periodic acid and reduced with $NaBH_4$ to the alcohol XVI. This compound can be incorporated into the polar area of phospholipids.

D-mannitol derivative (6 hydroxyl groups)

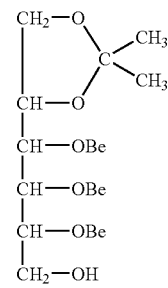

XV

D-lyxitol derivative (5 hydroxyl groups; from D-mannitol)

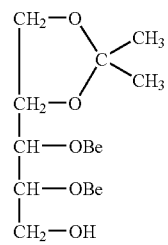

XVI

D-threitol derivative (4 hydroxyl groups; from D-mannitol)

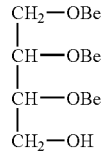

XVII

Model H: Polyhydric Alcohols with at Least 4 Hydroxyl Groups for Incorporation into the Polar Area of Phospholipids D-threitol Derivative The compound XVI is converted by way of benzylation into 1.2-isopropylidene-3.4.5-0.0.0-tribenyzl-D-lyxitol. After splitting off the isopropylidene protective group, periodic acid cleavage and reduction to the alcohol, one obtains XVII. This compound can be incorporated into the polar area of phospholipids in the usual way.

Phospholipids Which Contain Oligoglycerols in the Polar Area

In earlier publications we have described how phospholipids can be easily prepared from diacyl glycerols with saturated and unsaturated fatty acid chains, with two identical or two different fatty acid chains (DE 32 39 817 Ar, P. Woolley et al. Chem. Phys. Lipids 47 (1988) 55-62; H. Eibl et al., Chem. Phys. Lipids 47 (1988) 63-68). It is also possible to use acyl/alkyl or alkyl/acyl glycerols as starting product. However, phospholipids which contain dialkyl glycerols are metabolically extremely stable and resorption is negligible.

Basically, the compounds referred to can be prepared according to two different methods. This derives from the fact that a phosphoric acid diester is to be prepared from two alcohols, $R_1$—OH and $R_2$—OH.

The $R_1$—OH alcohols are alcohols which contain a glycerol backbone with two fatty acid chains and a free hydroxyl group. They can also have just one fatty acid chain and an additional protective group, usually benzyl, for the preparation of monoacrylic phospholipids; $R_1$—OH can, however, also stand for an alcohol with a simple alkyl group with one or two cis double bonds.

The $R_2$—OH alcohols are alcohols which have so far been designated as $G_2$, $G_3$ and $G_4$ in the text. They are described by the structural formulae III and V (for $G_2$), VII and VIII (for $G_3$) and X to XIV (for $G_4$). In like manner, use can also be made of the sugar alcohol derivatives XV to XVII.

Model G describes how two alcohols $R_1$—OH and $R_2$—OH can be utilized to prepare good yields of phosphoric acid diesters.

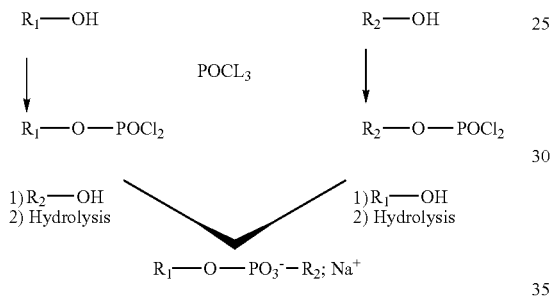

Where, for example, $R_1$=1.2-dipalmitoyl-sn-G and $R_2$=formula XI, the following structure is obtained after removal of the protective groups:

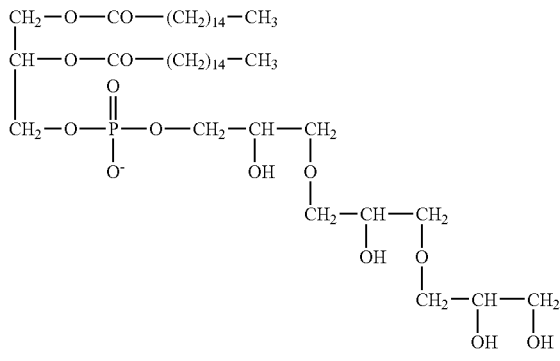

Model G: Phosphoric Acid Diester with the Formula $R_1O$—$PO_3^-$—$R_2$; $Na^+$

Phosphorus oxychloride is used as phosphorylation agent. From the two alcohols $R_1OH$ and $R_2OH$ to be linked via phosphate, one first of all prepares the corresponding phosphoric acid dichloride; this is reacted in each case with the other alcohol to phosphoric acid monochloride. Slightly acid hydrolysis then leads to the phosphoric acid diesters, which, after the protective groups have been split off, form, eg, the salt XVIII, 1.2-dipalmitoyl-sn-glycero-3-phospho-$G_1$-$G_2$-$G_3$-$G_4$; $Na^+$.

The following list of examples can be extended at will by using different combinations of fatty acid chains or by introducing additional fatty acids, both of synthetic and natural origin. If necessary in order to obtain particular properties, the phosphatidyl-oligoglycerols can contain additional alkyl chains or fatty acid residues in the oligoglycerol part.

The oligoglycerol-based methods described here can thus be used and modified in manifold ways in order to vary and influence the properties of liposomes. By analogy with the hexadecylphosphocholines and the erucylphosphocholines, however, these substances may also be important biologically active molecules which influence signal transduction and thus functional pathways in the cells.

Examples of phospho-$G_1$-$G_2$ compounds 1. 1.2-dipalmitoyl-sn-glycero-3-phospho-$G_1$-$G_2$;
   $Na^+$ salt:   $C_{41}H_{80}NaO_{12}P$   (819.04)
2. 1.2-dimyristoyl-sn-glycero-3-phospho-$G_1$-$G_2$;
   $Na^+$ salt:   $C_{37}H_{72}NaO_{12}P$   (762.93)
3. 1.2-distearoyl-sn-glycero-3-phospho-$G_1$-$G_2$;
   $Na^+$ salt:   $C_{45}H_{88}NaO_{12}P$   (875.14)
4. 1-palmitoyl-2-lauroyl-sn-glycero-3-phospho-$G_1$-$G_2$;
   $Na^+$ salt:   $C_{37}H_{72}NaO_{12}P$   (762.93)
5. 1-stearoyl-2-lauroyl-sn-glycero-3-phospho-$G_1$-$G_2$;
   $Na^+$ salt:   $C_{39}H_{76}NaO_{12}P$   (790.98)
6. 1.2-dioleoyl-sn-glycero-3-phospho-$G_1$-$G_2$;
   $Na^+$ salt:   $C_{45}H_{84}NaO_{12}P$   (871.11)
7. 1.2-dierucyl-sn-glycero-3-phospho-$G_1$-$G_2$;
   $Na^+$ salt:   $C_{53}H_{100}NaO_{12}P$   (983.32)
8. 1-stearoyl-2-oleoyl-sn-glycero-3-phospho-$G_1$-$G_2$;
   $Na^+$ salt:   $C_{45}H_{86}NaO_{12}P$   (873.13)
9. 1-palmitoyl-2-oleoyl-sn-glycero-3-phospho-$G_1$-$G_2$;
   $Na^+$ salt:   $C_{43}H_{82}NaO_{12}P$   (845.07)
10. 1-stearoyl-2-myristoyl-sn-glycero-3-phospho-$G_1$-$G_2$;
    $Na^+$ salt:   $C_{41}H_{80}NaO_{12}P$   (819.04)
11. 1-stearoyl-2-palmitoyl-sn-glycero-3-phospho-$G_1$-$G_2$;
    $Na^+$ salt:   $C_{43}H_{84}NaO_{12}P$   (847.09)
12. 1-myristoyl-sn-glycero-3-phospho-$G_1$-$G_2$;
    $Na^+$ salt:   $C_{23}H_{46}NaO_{11}P$   (552.57)
13. 1-palmitoyl-sn-glycero-3-phospho-$G_1$-$G_2$;
    $Na^+$ salt:   $C_{25}H_{50}NaO_{11}P$   (580.62)
14. 1-stearoyl-sn-glycero-3-phospho-$G_1$-$G_2$;
    $Na^+$ salt:   $C_{27}H_{54}NaO_{11}P$   (608.68)
15. Erucyl-phospho-$G_1$-$G_2$;
    $Na^+$ salt:   $C_{28}H_{56}NaO_8P$   (574.71)
16. Octadecyl-phospho-$G_1$-$G_2$;
    $Na^+$ salt:   $C_{24}H_{50}NaO_8P$   (520.62)
17. Hexadecyl-phospho-$G_1$-$G_2$;
    $Na^+$ salt:   $C_{22}H_{46}NaO_8P$   (492.56)
18. Tetradecyl-phospho-$G_1$-$G_2$;
    $Na^+$ salt:   $C_{20}H_{42}NaO_8P$   (464.51)
19. Oleyl-phospho-$G_1$-$G_2$;
    $Na^+$ salt:   $C_{24}H_{48}NaO_8P$   (518.60)
20. 1-O-octadecyl-2-O-methyl-sn-glycero-3-phospho-$G_1$-$G_2$;
    $Na^+$ salt:   $C_{28}H_{58}NaO_{10}P$   (608.72)

Examples of phospho-$G_1$-$G_2$-$G_3$ compounds 1. 1.2-dipalmitoyl-sn-glycero-3-phospho-$G_1$-$G_2$-$G_3$;
   $Na^+$ salt:   $C_{44}H_{86}NaO_{14}P$   (893.12)
2. 1.2-distearoyl-sn-glycero-3-phospho-$G_1$-$G_2$-$G_3$;
   $Na^+$ salt:   $C_{48}H_{94}NaO_{14}P$   (949.22)
3. 1-palmitoyl-2-lauroyl-sn-glycero-3-phospho-$G_1$-$G_2$-$G_3$;
   $Na^+$ salt:   $C_{40}H_{78}NaO_{14}P$   (837.01)
4. 1-stearoyl-2-lauroyl-sn-glycero-3-phospho-$G_1$-$G_2$-$G_3$;
   $Na^+$ salt:   $C_{42}H_{82}NaO_{14}P$   (865.06)
5. 1.2-dioleoyl-sn-glycero-3-phospho-$G_1$-$G_2$-$G_3$;
   $Na^+$ salt:   $C_{48}H_{90}NaO_{14}P$   (945.19)
6. 1.2-dierucyl-sn-glycero-3-phospho-$G_1$-$G_2$-$G_3$;
   $Na^+$ salt:   $C_{56}H_{106}NaO_{14}P$   (1057.40)
7. 1-stearoyl-2-oleoyl-sn-glycero-3-phospho-$G_1$-$G_2$-$G_3$;
   $Na^+$ salt:   $C_{48}H_{92}NaO_{14}P$   (947.21)
8. 1-palmitoyl-2-oleoyl-sn-glycero-3-phospho-$G_1$-$G_2$-$G_3$;
   $Na^+$ salt:   $C_{46}H_{88}NaO_{14}P$   (919.148)

-continued 9. 1-stearoyl-sn-glycero-3-phospho-$G_1$-$G_2$-$G_3$;
    Na$^+$ salt:   $C_{30}H_{60}NaO_{13}P$   (682.76)
10. Erucyl-phospho-$G_1$-$G_2$-$G_3$;
    Na$^+$ salt:   $C_{31}H_{62}NaO_{10}P$   (648.79)
11. Octadecyl-phospho-$G_1$-$G_2$-$G_3$;
    Na$^+$ salt:   $C_{27}H_{56}NaO_{10}P$   (594.69)
12. Hexadecyl-phospho-$G_1$-$G_2$-$G_3$;
    Na$^+$ salt:   $C_{25}H_{52}NaO_{10}P$   (566.64)
13. 3-O-octadecyl-2-O-methyl-sn-glycero-1-phospho-$G_1$-$G_2$-$G_3$;
    Na$^+$ salt:   $C_{31}H_{64}NaO_{12}P$   (682.80)

Examples of phospho-$G_1$-$G_2$-$G_3$-$G_4$ compounds 1. 1.2-dipalmitoyl-sn-glycero-3-phospho-$G_1$-$G_2$-$G_3$-$G_4$;
    Na$^+$ salt:   $C_{47}H_{92}NaO_{16}P$   (967.20)
2. 1.2-distearoyl-sn-glycero-3-phospho-$G_1$-$G_2$-$G_3$-$G_4$;
    Na$^+$ salt:   $C_{51}H_{100}NaO_{16}P$   (1023.30)
3. 1-stearoyl-2-lauroyl-sn-glycero-3-phospho-$G_1$-$G_2$-$G_3$-$G_4$;
    Na$^+$ salt:   $C_{45}H_{88}NaO_{16}P$   (939.14)
4. 1.2-dioleoyl-sn-glycero-3-phospho-$G_1$-$G_2$-$G_3$-$G_4$;
    Na$^+$ salt:   $C_{51}H_{96}NaO_{16}P$   (1019.27)
5. 1.2-dierucyl-sn-glycero-3-phospho-$G_1$-$G_2$-$G_3$-$G_4$;
    Na$^+$ salt:   $C_{59}H_{112}NaO_{16}P$   (1131.48)
6. 1-stearoyl-2-oleoyl-sn-glycero-3-phospho-$G_1$-$G_2$-$G_3$-$G_4$;
    Na$^+$ salt:   $C_{51}H_{98}NaO_{16}P$   (1021.29)
7. Erucyl-phospho-$G_1$-$G_2$-$G_3$-$G_4$;
    Na$^+$ salt:   $C_{34}H_{68}NaO_{12}P$   (722.87)

Examples of phospho-sn-$G_1$ compounds
sn-1-$G_1$-$G_2$:

1. 1.2-dipalmitoyl-sn-glycero-3-phospho-sn-1-$G_1$-$G_2$;
    Na$^+$ salt:   $C_{41}H_{80}NaO_{12}P$   (819.04)
2. 1.2-distearoyl-sn-glycero-3-phospho-sn-1-$G_1$-$G_2$;
    Na$^+$ salt:   $C_{45}H_{88}NaO_{12}P$   (875.14)
3. 1-stearoyl-2-lauroyl-sn-glycero-3-phospho-sn-1-$G_1$-$G_2$;
    Na$^+$ salt:   $C_{39}H_{76}NaO_{12}P$   (790.98)
4. 1-stearoyl-2-oleoyl-sn-glycero-3-phospho-sn-1-$G_1$-$G_2$;
    Na$^+$ salt:   $C_{45}H_{86}NaO_{12}P$   (873.13)

sn-1-$G_1$-$G_2$-$G_3$:

1. Dipalmitoyl-sn-glycero-3-phospho-sn-1-$G_1$-$G_2$-$G_3$;
    Na$^+$ salt:   $C_{44}H_{86}NaO_{14}P$   (893.12)
2. 1.2-distearoyl-sn-glycero-3-phospho-sn-1-$G_1$-$G_2$-$G_3$;
    Na$^+$ salt:   $C_{48}H_{94}NaO_{14}P$   (949.22)

sn-1-$G_1$-$G_2$-$G_3$-$G_4$:

1. 1.2-dipalmitoyl-sn-glycero-3-phospho-sn-1-$G_1$-$G_2$-$G_3$-$G_4$;
    Na$^+$ salt:   $C_{47}H_{92}NaO_{16}P$   (967.20)
2. 1.2-distearoyl-sn-glycero-3-phospho-sn-1-$G_1$-$G_2$-$G_3$-$G_4$;
    Na$^+$ salt:   $C_{51}H_{100}NaO_{16}P$   (1023.30)

Examples of linkages with sugar alcohols
Phospho-D-mannitol compounds 1. 1.2-dipalmitoyl-sn-glycero-3-phospho-D-mannitol;
    Na$^+$ salt:   $C_{41}H_{80}NaO_{13}P$   (835.03)
2. 1.2-distearoyl-sn-glycero-3-phospho-D-mannitol;
    Na$^+$ salt:   $C_{45}H_{88}NaO_{13}P$   (891.13)
3. 1-palmitoyl-2-lauroyl-sn-glycero-3-phospho-D-mannitol;
    Na$^+$ salt:   $C_{37}H_{72}NaO_{13}P$   (788.92)
4. 1-stearoyl-2-lauroyl-sn-glycero-3-phospho-D-mannitol;
    Na$^+$ salt:   $C_{39}H_{76}NaO_{13}P$   (806.97)
5. 1-stearoyl-2-myristoyl-sn-glycero-3-phospho-D-mannitol;
    Na$^+$ salt:   $C_{41}H_{80}NaO_{13}P$   (835.03)
6. 1-stearoyl-sn-glycero-3-phospho-D-mannitol;
    Na$^+$ salt:   $C_{27}H_{54}NaO_{12}P$   (624.67)
7. Octadecyl-phospho-D-mannitol;
    Na$^+$ salt:   $C_{24}H_{50}NaO_{9}P$   (536.61)
8. 1-O-octadecyl-2-O-methyl-sn-glycero-3-phospho-D-mannitol;
    Na$^+$ salt:   $C_{28}H_{58}NaO_{11}P$   (624.71)

Phospho-D-lyxitol compounds 1. 1.2-dipalmitoyl-sn-glycero-3-phospho-D-lyxitol;
    Na$^+$ salt:   $C_{40}H_{78}NaO_{12}P$   (805.00)
2. 1.2-distearoyl-sn-glycero-3-phospho-D-lyxitol;
    Na$^+$ salt:   $C_{44}H_{86}NaO_{12}P$   (861.10)
3. 1-palmitoyl-2-lauroyl-sn-glycero-3-phospho-D-lyxitol;
    Na$^+$ salt:   $C_{36}H_{70}NaO_{12}P$   (758.89)
4. 1-stearoyl-2-lauroyl-sn-glycero-3-phospho-D-lyxitol;
    Na$^+$ salt:   $C_{38}H_{74}NaO_{12}P$   (776.94)
5. 1-stearoyl-2-myristoyl-sn-glycero-3-phospho-D-lyxitol;
    Na$^+$ salt:   $C_{40}H_{78}NaO_{12}P$   (805.00)

Phospho-D-threitol compounds 1. 1.2-dipalmitoyl-sn-glycero-3-phospho-D-threitol;
    Na$^+$ salt:   $C_{39}H_{76}NaO_{11}P$   (774.97)
2. 1.2-distearoyl-sn-glycero-3-phospho-D-threitol;
    Na$^+$ salt:   $C_{43}H_{84}NaO_{11}P$   (831.07)
3. 1-stearoyl-2-lauroyl-sn-glycero-3-phospho-D-threitol;
    Na$^+$ salt:   $C_{37}H_{72}NaO_{11}P$   (746.91)
4. 1-stearoyl-2-myristoyl-sn-glycero-3-phospho-D-threitol;
    Na$^+$ salt:   $C_{39}H_{76}NaO_{11}P$   (774.97)

EXAMPLE 4h

Phosphorylation Steps (General Directions) Based, by Way of Example, on the Isolation of 1.2-dipalmitoyl-sn-glycero-3-phospho-glyceroglycerol, Na$^+$ Salt POCl$_3$ (0.1 mol-15.3 g) in 15 ml THF is introduced into a three-necked flask. While vigorously stirring the contents of the ice-cooled flask, one adds—dropwise—1.2-dipalmitoyl-sn-glycerol (0.1 mol-57 g) in 100 ml THF and, separately, triethylamine (0.11 mol-11 g) in such manner that there is always a slight excess of triethylamine compared to 1.2-dipalmitoyl-sn-glycerol, which takes up the HCl as it forms. The temperature of the reaction mixture should not exceed 16° C. On completion of the addition, the reaction mixture is left to stand for a further 30 minutes at 16° C. and then subjected to a TLC check to make sure that the reaction is complete (1.2-dipalmitoyl-sn-glycerol, R$_f$ 0.8; 1.2-dipalmitoyl-sn-glycero-3-phosphoric acid dichloride is converted by way of methanolysis to the corresponding phosphoric acid dimethyl ester, R$_f$ 0.4 in ether.)

The second phosphorylation step is carried out with a protected oligoglycerol. Here, the conversion with 2-O-benzyl-rac-G$_1$-1.3-0.0-1.2-isopropylidene-rac-G$_2$ is described. To the reaction mixture with 1.2-dipalmitoyl-sn-glycero-3-phosphoric acid dichloride one adds—dropwise—the above alcohol (0.105 mol-31 g) and triethylamine (0.13-13 g) in 100 ml THF in such manner that the temperature of the reaction mixture does not exceed 40° C. After 3 hours at 40° C. the reaction is complete (starting product phosphoric acid dimethyl ester, R$_f$ 0.4; product methyl ester, R$_f$ 0.7 in ether). One removes the trethylamine hydrochloride precipitate by filtration and hydrolyses the reaction mixture, mainly 1.2-dipalmitoyl-sn-glycero-3-phospho-2-O-benzyl-rac-glycerol-1.3-0.0-1.2-isopropylidene-rac-glycerol-monochloride together with incompletely reacted 1.2-dipalmitoyl-sn-glycero-3-phosphoric acid dichloride, with 26 g Na$_2$CO$_3$ dissolved in 260 ml H$_2$O. After 4 hours, 400 ml diisopropyl ether are added and the upper phase, which contains the product, rotated in an evaporator until crystals begin to form. 500 ml acetone are now added, and the crystals formed removed under suction at 20° C. The filtrate contains the protected phosphatidylglyceroglycerol, Na$^+$ salt (R$_f$ 0.6 in CHCl$_3$/CH$_3$OH/glacial acetic acid/H$_2$O 600:60:20:5). After removal of the solvent, one obtains 48 g crude product, which is heated in 140 ml acetic acid and 60 ml H₂O for 30 minutes to 60-70° C. (cleavage of the isopropylidene protective group). One then adds 500 ml CHCl₃, 600 ml CH₃OH and 400 ml H₂O and shakes thoroughly. The lower CHCl₃ phase is washed again with 600 ml CH₃OH and 500 ml H₂O, with addition of sufficient Na₂CO₃ to obtain a pH of 6 in the aqueous phase. The lower chloroform phase is rotated in an evaporator and the residue taken up in 400 ml THF. To remove the benzyl protective group, the solution has 6 g Pd/C added to it and is de-benzylated in a H₂ atmosphere. The reaction is complete after about 4 hours. The catalyst is separated off by filtration, the solvent removed and the residue (~30 g) taken up in 100 ml CHCl₃. 900 ml acetone are added, and the crystals formed removed under suction. One obtains a white powder; 1.2-dipalmitoyl-sn-glycero-3-phospho-glyceroglycerol, Na⁺ salt, yield: 26 g (~32%).

Empirical formula: $C_4$, $H_{80}NaO_{12}P$ (MW 819.04) calculated: C, 60.13; H, 9.85; Na, 2.81; O, 23.44; P, 3.78 measured: C, 60.01; H, 9.79; Na, -; O, -; P, 3.69

1.2-dipalmitoyl-sn-glycero-3-phospho-glycero-glycero-glycero, Na⁺ Salt

Empirical formula: $C_{44}H_{86}NaO_{14}P$ (MW 893.12) calculated: C, 59.17; H, 9.71; Na, 2.57; O, 25.08; P, 3.47 measured: C, 59.11; H, 9.62; Na, -; O, -; P, 3.45

1.2-dipalmitoyl-sn-glycero-3-phospho-glycero-glycero-glycerol, Na⁺ Salt

Empirical formula: $C_{47}H_{92}NaO_{16}P$ (MW 967.20) calculated: C, 58.37; H, 9.59; Na, 2.38; O, 26.47; P, 3.20 measured: C, 58.29; H, 9.53; Na, -; O, -; P, 3.19

To prepare phosphatidyl-oligoglycerols with an aliphatic chain, the so-called lysophosphatidyl-oligoglycerols, one can start with compounds which have a benzyl ether group in the sn-2 position of the glycerol, eg, 1-palmitoyl-2-O-benzyl-sn-glycerol, 1-stearoyl-2-O-benzyl-sn-glycerol, 1-O-hexadecyl-2-O-benzyl-sn-glycerol, 1-O-octadecyl-2-O-benzyl-sn-glycerol etc. We have described the preparation of these compounds in the publications H. Eibl and P. Woolley, Chem. Phys. Lipids 41 (1986) 53-63 and Chem. Phys. Lipids 47 (1988) 55-62. They are phosphorylated in the manner described for the preparation of 1.2-dipalmitoyl-sn-glycero-3-phospho-glyceroglycerol, Na⁺ salt, and reacted with the protected oligoglycerols. The protective groups are split off analogously. In the last step, by means of catalytic hydrogenolysis with Pd/C (5% on activated charcoal) the benzyl groups are split off both the oligoglycerol part and the glycerol, which carries an acyl or alkyl group (see the examples).

Preparation of the alkylphospho-oligoglycerols is easy by comparison, as in this case the corresponding alcohols are reacted according to the given phosphorylation pattern. To obtain the unsaturated sorts, however, one must use tetrahydropyranyl instead of benzyl as protective group.

A different strategy altogether is employed to synthesize the unsaturated representatives of this substance group. 1.2-dibenzyl-sn-glycerol is phosphorylated in the described manner (see, in addition, German patent application DE 32 39 817), then reacted with a tetrahydropyranyl-protected oligoglycerol. Instead of the hydrolysis, a methanolysis is performed and phosphoric acid triesters obtained, eg, for 2-O-tetrahydropyranyl-rac-G₁-1.3-0.0-1.2-isopropylidene-rac-G₂;

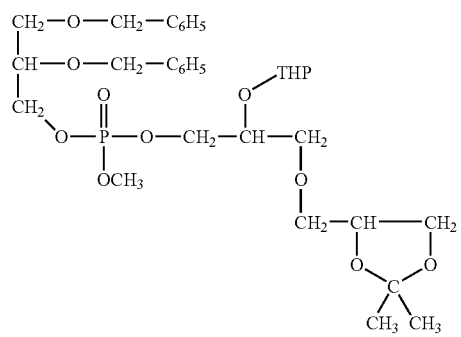

This key intermediate is now subjected to hydrolysis with Pd/C (5% on activated charcoal). One obtains:

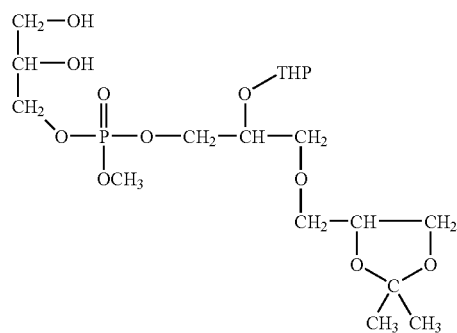

It is now possible to introduce arbitrary unsaturated and saturated fatty acids at the sn-1 and sn-2 positions of the glycerol molecule. This step is followed, as described in our earlier patent application, by splitting off the methyl group with LiBr and then hydrolysing the isopropylidene and tetrahydropyranyl protective groups in 70% acetic acid at 60 to 70° C. The dioleoyl compounds do not crystallize readily and must therefore be purified chromatographically; the dierucyl compounds, by contrast, are obtained easily in cristalline form.

The phosphoric acid triester strategy is also recommended for preparing mixed-chain phosphatidyl-oligoglycerols. In this case, as with the synthesis of lysophosphatidyloligoglycerols, 1-acyl-2-O-benzyl-sn-glycerols or 1-O-alkyl-2-O-benzyl-sn-glycerols are used as starting products and reacted analogously to 1.2-dibenzyl-sn-glycerol. Following catalytic debenzylation one obtains as intermediates for the G₂ compound:

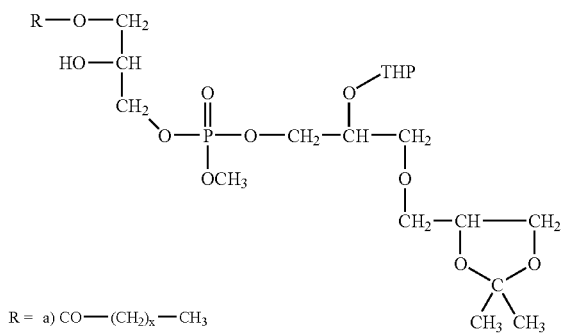

Unsaturated fatty acids can now be introduced at the free sn-2 position, and the molecule freed from its protective groups as described. It is convenient that molecules with the fatty acid combination 1-palmitoyl-2-oleoyl- or 1-stearoyl-2-oleoyl crystallize readily.

EXAMPLE 5

Additional Properties

As the number of glycerol molecules increases, the number of free hydroxyl groups and thus also the polarity increases. For a proportion of 5% in water, PP-G-PG$_4$ is the only PP-G-PG$_n$ to form a clear isotropic solution. The lipids PP-G-PG$_1$, PP-G-PG$_2$ and PP-G-PG$_3$ dissolve when heated above 40° C. in water and form superstructures. When the temperature falls below 40° C., lamellar structures with differently pronounced hystereses are formed, which are recognizable on account of their anisotropy (birefraction in polarized light). The PP-G-PG$_1$ solution becomes cloudy most quickly, and excess lipid precipitates when the solution is left to stand at room temperature. The lamellar phases of PP-G-PG$_2$ and PP-G-PG$_3$ remain stable even at low temperatures (down to 4° C.). Whereas the transition from the isotropic to the anisotropic phase at room temperature is recognizable after a few minutes with PP-G-PG$_2$, it takes several hours for PP-G-PG$_3$. The differences in polarity are also evident from the different retention factors (R$_f$) in the thin-layer chromatogram on silica gel.

What is claimed is:

1. A compound represented by the formula:

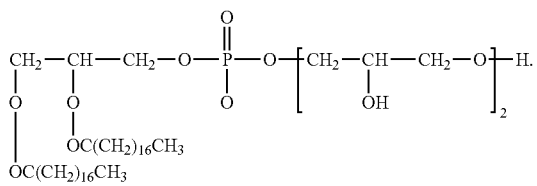

2. A compound represented by the formula:

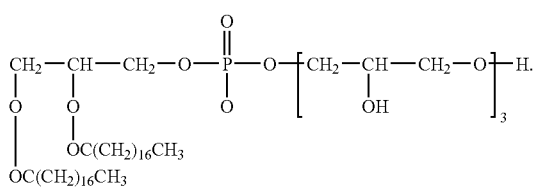

3. A liposome comprising a phospholipid, alkyl phospholipid, or cholesterol, and 1 to 50 mol % of a compound selected from the group consisting of:

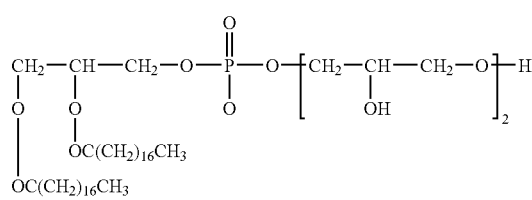

and

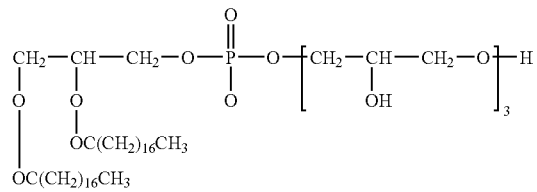

or salts thereof;

provided that when the liposome contains a phospholipid, the phospholipid and the compound contain the same fatty acid residues.

4. The liposome of claim 3, wherein the liposome contains 5 to 15 mol % of the compound.

5. A pharmaceutical composition comprising a liposome and a pharmaceutical drug, said liposome comprising a phospholipid, alkyl phospholipid, or cholesterol, and 1 to 50 mol % of a compound of formula (A):

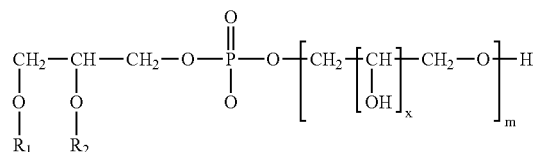

or salts thereof;

wherein R$_1$ and R$_2$ are independently hydrogen or a saturated or unsaturated C$_8$-C$_{24}$ alkyl or C$_8$-C$_{24}$ acyl residue, which may be branched or substituted;

x is a whole number from 1 to 4; and m is a whole number from 2 to 5;

wherein the compound of formula (A) is more than 90% uniform with respect to the value of m, provided that when the liposome contains a phospholipid, the phospholipid and the compound of formula (A) contain the same fatty acid residues, and wherein the pharmaceutical drug is entrapped within said liposome, and wherein the pharmaceutical drug is a member selected from the group consistiun of doxorubicin, epirubicin, daunomycin, idarubicin, hexadecylphosphocholine, 1-octadecyl-2-methyl-rac-glycero-3-phosphocholine, a cis-platinum complex, a mitomycin, a cytokine, an anti-mycotic substance, an anti-protozoal, amphotericin B, Taxol, miltefosin, edelfosin, and ilmofosin.

6. The pharmaceutical composition of claim 5, wherein said composition is combined with a pharmaceutical diluent, adjuvant, carrier medium, or filler.

7. The pharmaceutical composition of claim 5, wherein the cis-platinum complex is a member selected from the group consisting of carboplatin and novantron.

8. The phannaceutical composition of claim 5, wherein said cytokine is an interferon.

9. The pharmaceutical composition of claim 8, wherein the interferon is α-interferon.

10. The pharmaceutical composition of claim 5, wherein said antimycotic is amphotericin B.

11. The pharmaceutical composition of claim 5, wherein the compound of formula (A) is:

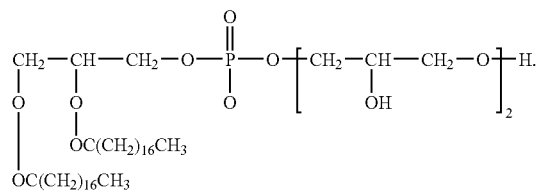
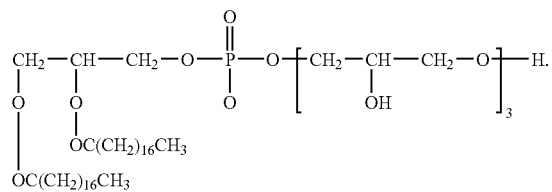
12. The pharmaceutical composition of claim 5, wherein the compound of formula (A) is:
* * * * *